(12) United States Patent
Dumont et al.

(10) Patent No.: US 10,314,882 B2
(45) Date of Patent: Jun. 11, 2019

(54) METHODS, USES AND COMPOSITIONS OF TIE2 AGONISTS

(71) Applicants: Sunnybrook Research Institute, Toronto (CA); UNITY HEALTH TORONTO, Toronto (CA)

(72) Inventors: Daniel Dumont, Oakville (CA); Paul Van Slyke, North York (CA); Warren Lee, Toronto (CA)

(73) Assignees: Sunnybrook Research Institute, Toronto, ON; Unity Health Toronto, Toronto, ON ( * ) Notice: Subject to any disclaimer, the term of this patent is extended or adjusted under 35 U.S.C. 154(b) by 203 days.

(21) Appl. No.: 14/783,261

(22) PCT Filed: Mar. 19, 2014

(86) PCT No.: PCT/CA2014/000269
§ 371 (c)(1),
(2) Date: Oct. 8, 2015

(87) PCT Pub. No.: WO2014/165963
PCT Pub. Date: Oct. 16, 2014

(65) Prior Publication Data
US 2016/0058828 A1    Mar. 3, 2016

Related U.S. Application Data

(60) Provisional application No. 61/810,879, filed on Apr. 11, 2013.

(51) Int. Cl.
| | |
|---|---|
| *A61K 38/08* | (2019.01) |
| *A61K 38/10* | (2006.01) |
| *A61K 38/16* | (2006.01) |
| *A61K 38/18* | (2006.01) |
| *A61P 31/12* | (2006.01) |
| *A61P 31/16* | (2006.01) |
| *C07K 7/06* | (2006.01) |
| *C07K 7/08* | (2006.01) |
| *C07K 14/515* | (2006.01) |
| *C07K 14/475* | (2006.01) |
| *A61K 31/13* | (2006.01) |
| *A61K 31/195* | (2006.01) |
| *A61K 31/7056* | (2006.01) |
| *A61K 31/215* | (2006.01) |
| *A61K 31/7012* | (2006.01) |
| *A61K 45/06* | (2006.01) |
| *A61K 47/60* | (2017.01) |
| *C07K 14/705* | (2006.01) |
| *C07K 14/71* | (2006.01) |
| *A61K 38/17* | (2006.01) |
| *A61K 38/00* | (2006.01) |

(52) U.S. Cl.
CPC .............. *A61K 38/08* (2013.01); *A61K 31/13* (2013.01); *A61K 31/195* (2013.01); *A61K 31/215* (2013.01); *A61K 31/7012* (2013.01); *A61K 31/7056* (2013.01); *A61K 38/10* (2013.01); *A61K 38/1891* (2013.01); *A61K 45/06* (2013.01); *A61K 47/60* (2017.08); *A61P 31/12* (2018.01); *A61P 31/16* (2018.01); *C07K 7/06* (2013.01); *C07K 7/08* (2013.01); *C07K 14/515* (2013.01); *A61K 38/00* (2013.01); *A61K 38/16* (2013.01); *A61K 38/179* (2013.01); *A61K 38/18* (2013.01); *C07K 14/475* (2013.01); *C07K 14/705* (2013.01); *C07K 14/71* (2013.01)

(58) Field of Classification Search
CPC .... C07K 14/47; C07K 14/705; A61K 38/177; A61K 38/179; A61K 38/1891; A61K 38/17; A61K 38/18
See application file for complete search history.

(56) References Cited

U.S. PATENT DOCUMENTS

| | | |
|---|---|---|
| 6,365,154 B1 | 4/2002 | Holmes et al. |
| 6,455,035 B1 | 9/2002 | Suri et al. |
| 8,507,656 B2 | 8/2013 | Bedian et al. |
| 8,957,022 B2 | 2/2015 | Van Slyke et al. |
| 9,186,390 B2 | 11/2015 | Van Slyke et al. |
| 2005/0100906 A1 | 5/2005 | Davis et al. |
| 2007/0298996 A1 | 12/2007 | Koh et al. |

(Continued)

FOREIGN PATENT DOCUMENTS

| | | |
|---|---|---|
| WO | 0037642 A1 | 6/2000 |
| WO | 0147951 A2 | 7/2001 |

(Continued)

OTHER PUBLICATIONS

Chattopadhyay et al. Recent advancements for the evaluation of anti-viral activities of natural products. New Biotech 25(5): 347-368, 2009.*

(Continued)

*Primary Examiner* — Bridget E Bunner
(74) *Attorney, Agent, or Firm* — Bereskin & Parr LLP; Melanie Szweras

(57) ABSTRACT

The present disclosure provides methods and uses of Tie2 agonists alone or in combination with antiviral agents. In particular, the present disclosure provides methods and uses for treating influenza, treating a bacterial superinfection associated with influenza and decreasing lung endothelial leakage. The disclosure also provides compositions comprising (a) a Tie2 agonist and (b) an antiviral agent and methods and uses thereof.

28 Claims, 14 Drawing Sheets
Specification includes a Sequence Listing.

(56) References Cited

U.S. PATENT DOCUMENTS

| | | | |
|---|---|---|---|
| 2011/0097300 A1* | 4/2011 | Van Slyke | A61K 38/1709 424/85.1 |
| 2011/0268694 A1 | 11/2011 | Shalwitz et al. | |
| 2013/0172234 A1 | 7/2013 | Van Slyke et al. | |
| 2015/0202251 A1 | 7/2015 | Van Slyke et al. | |
| 2016/0151448 A1 | 6/2016 | Van Slyke et al. | |

FOREIGN PATENT DOCUMENTS

| | | |
|---|---|---|
| WO | 03106501 A1 | 12/2003 |
| WO | 06005361 A1 | 1/2006 |
| WO | 2008/049227 A1 | 5/2008 |
| WO | 2009/114539 A2 | 9/2009 |
| WO | 2010/010551 A2 | 1/2010 |
| WO | 2010/081172 A1 | 7/2010 |
| WO | 2011/134056 A1 | 11/2011 |

OTHER PUBLICATIONS

Seegar et al. Tie1-Tie2 interactions mediate functional differences between angiopoietin ligands. Molec Cell 37: 643-655, 2010.*

Aeffner et al. Mouse models of acute respiratory distress syndrome: a review of analytical approaches, pathologic features, and common measurements. Toxicol Pathol 43: 1074-1092, 2015.*

Armstrong et al. Influenza infects lung microvascular endothelium leading to microvascular leak: role of apoptosis and claudin-5. PLoS One 7(10): e47323, 2012 (14 total pages).*

Chan et al. Human mesenchymal stromal cells reduce influenza A H5N1—associated acute lung injury in vitro and in vivo. Proc Natl Acad Sci USA 113(13): 3621-3626, 2016.*

Chao et al. "The Role of Inflammation and Blood Cells in Wound Healing" in The ACL Handbook: Knee Biology, Mechanics, and Treatment (2013) New York: Springer Science + Business Media, pp. 73-89.

Cho et al. "Designed angiopoietin-1 variant, COMP-Ang1, protects against radiation-induced endothelial cell apoptosis", PNAS, Apr. 13, 2004, vol. 101, No. 15, pp. 5553-5558.

Tsigkos et al. "Angiopoietins in angiogenesis and beyond", Expert Opin. Investig. Drugs, 2003, vol. 12, No. 6, pp. 1-9.

Ward, N.L. and Dumont, D.J., "The angiopoietins and Tie2/Tek: adding to the complexity of cardiovascular development", Semin. Cell Dev. Biol., 2002, vol. 13, pp. 19-27.

Darwish, I. et al., "Immunomodulatory therapy for severe influenza", Expert Rev. Anti Infect. Ther., 2011, vol. 9, No. 7, pp. 807-822.

Armstrong, S. M. et al., "The lung microvascular endothelium as a therapeutic target in severe influenza", Antiviral Research, 2013, vol. 99, pp. 113-118.

"Influenza and lung microvascular leak", Powerpoint, presented in Toronto at the University of Toronto Respirology Research-In-Progress Rounds, Jun. 22, 2012.

Armstrong et al. "Influenza Infects Lung Microvascular Endothelium Leading to Microvascular Leak: Role of Apoptosis and Claudin-5", PLOS One, Oct. 2012, vol. 7: pp. 1-14.

Armstrong et al. "Influenza Infects Human Lung Microvascular Endothelium Leading to Microvascular Leak: Role of Apoptosis and Claudin-5", Presentation, presented in San Francisco at the Annual Meeting of the American Thoracic Society, May 21, 2012.

Kumpers et al. "The synthetic Tie2 agonist peptide vasculotide protects against vascular leakage and reduces mortality in murine abdominal sepsis", Critical Care, 2011, vol. 15: pp. 1-14.

Baranovich, T. et al. "The Neuraminidase Inhibitor Oseltamivir is Effective Against A/Anhui/1/2013 (H7N9) Influenza Virus in a Mouse Model of Acute Respiratory Distress Syndrome", The Journal of Infectious Diseases, Nov. 7, 2013, pp. 1-11.

Sidwell et al. "Inhibition of influenza virus infections in mice by GS4104, an orally effective influenza virus neuraminidase inhibitor", Antiviral Research, 1998, vol. 37: pp. 107-120.

Wu et al. "Vasculotide Reduces Endothelial Permeability and Tumor Cell Extravasation in the Absence of Binding to or Agonistic Activation of Tie2", EMBO Molecular Medicine, Apr. 7, 2015, pp. 1-18.

David, Sascha et al. "Effects of a synthetic PEG-ylated Tie-2 agonist peptide on endotoxemic lung injury and mortality", Am J Physiol Lung Cell Mol Physiol, 2011, vol. 300, pp. L851-L862.

Cho et al. "COMP-Ang1: A designed angiopoietin-1 variant with nonleaky angiogenic activity" PNAS, 2004, 101(15), 5547-5552.

Cho et al. "COMP-angiopoietin-1 promotes wound healing through enhanced angiogenesis, lymphangiogenesis and blood flow in a diabetic mouse model" PNAS, Mar. 28, 2006, 103(13), 4946-4951.

Kim et al. "Oligomerization and multimerization are critical for angiopoietin-1 to bind and phosphorylate Tie2", The Journal of Biological Chemistry, 2005, 280(20), 20126-20131.

Kim et al. "COMP-angiopoietin ameliorates renal fibrosis in a unilateral ureteral obstruction model" Journal of the American Society of Nephrology, 2006, 17, 2474-2483.

Kwak et al. "Angiopoietin-1 inhibits irradiation- and mannitol-induced apoptosis in endothelial cells" Circulation, 2000, 101, 2317-2324.

Peirce et al. "Spatial and temporal control of angiogenesis and arterialization using applications of VEGF164 and Ang-1" Am. J. Physiol. Heart Circ. Physiol., 2004, 286, H918-H925.

Procopio et al. "Angiopoietin-1 and -2 coiled domains mediate distinct homo-oligomerization patterns but fibrinogen-like domains mediate ligand activity" The Journal of Biological Chemistry, 1999, 274(42), 30196-30201.

Wu et al. "A novel small peptide as a targeting ligand for receptor tyrosine kinase Tie2" Biochemical and Biophysical Research Communications, 2004, 315, 1004-1010.

Tournaire et al. "A short synthetic peptide inhibits signal transduction, migration and angiogenesis mediated by Tie2 receptor", EMBO reports, vol. 5, No. 3, 2004.

Ward et al. "Functional inhibition of secreted angiopoietin: a novel role for angiopoietin 1 in coronary vessel patterning", Biochemical and Biophysical Research Communications 323 (2004) 937-946.

Davis et al. "Angiopoietins have distinct modular domains essential for receptor binding, dimerization and superclustering", Nature structural Biology, vol. 10, No. 1, Jan. 2003.

Simoes, D.C.M. et al. "Angiopoietin-1 protects against airway inflammation and hyperreactivity in asthma". Am. J. Respir. Crit. Care Med. Mar. 20, 2008 (Mar. 20, 2008). vol. 177, pp. 1314-1321.

Kanazawa, H. et al. "Angiopoietin-2 as a contributing factor of exercise-induced bronchoconstriction in asthmatic patients receiving inhaled corticosteroid therapy". J. Allergy Clin. Immunol. Feb. 2008 (Feb. 2008). vol. 121, pp. 390-395.

Makinde, T. and Agrawal, D.K. "Intra and extravascular transmembrane signalling of angiopoietin-1-Tie2 receptor in health and disease". J. Cell Mol. Med. Jun. 2008 (Jun. 2008). vol. 12, No. 3, pp. 810-828.

Kuroda, K. et al. "Altered expression of angiopoietins and Tie2 endothelium receptor in psoriasis". J. Invest. Dermatol. May 2001 (May 2001). vol. 116, No. 5, pp. 713-720.

Wells, T.N.C. et al. "Chemokine blockers—therapeutics in the making?" TRENDS in Pharmacological Sciences, vol. 27, No. 1, Jan. 2006, pp. 41-47.

Lee, S. et al. "Protective effect of COMP-angiopoietin-1 on cyclosporine-induced renal injury in mice". Nephrol. Dial. Transplant (2008) 23:2784-2794.

Lee, K.S. et al. "Blockade of airway inflammation and hyper-responsiveness by an angiopoietin-1 variant, COMP-Ang1". Experimental and Molecular Medicine, vol. 39, No. 6, 733-745, Dec. 2007.

Vidal et al. "Making sense of antisense", Eur J Cancer 41: 2812-2818, 2005.

Van Slyke et al. "Acceleration of diabetic wound healing by an angiopoietin peptide mimetic", Tissue Engineering: Part A, 15(6): 1269-1280, published online Dec. 16, 2008.

Tokuriki et al. "Stability effects of mutations and protein evolvability", Curr Opin Structural Biol 19: 596-604, 2009.

Phillips, A.J. "The challenge of gene therapy and DNA delivery", J Pharm Pharmacology 53: 1169-1174, 2001.

Rubanyi, G.M. "The future of human gene therapy", Mol Aspects Med 22: 113-142, 2001.

(56) References Cited

OTHER PUBLICATIONS

Juengst, E.T. "What next for human gene therapy?", BMJ 326: 1410-1411, 2003.
Pirollo et al. "Targeted delivery of small interfering RNA: approaching effective cancer therapies", Cancer Res 68(5): 1247-1250, Mar. 2008.
Brenner, S.E., "Errors in genome annotation", Trends in Genetics, 15(4): 132-133, 1999.
Bork et al. "Go hunting in sequence databases but watch out for the traps", Trends in Genetics, 12(10): 425-427, Oct. 1996.
Wells, J.A. "Additivity of mutational effects in proteins", Biochemistry 29(37): 8509-8517, Sep. 18, 1990.
Ngo et al. "Computational complexity, protein structure prediction, and the Levinthal paradox", The Protein Folding Problem and Tertiary Structure Prediction, pp. 491-495, 1994.
Skolnick et al. "From genes to protein structure and function: novel applications of computational approaches in the genomic era", Trends in Biotech, 18(1): 34-39, 2000.
Bork, P. "Powers and pitfalls in sequence analysis: the 70% hurdle", Genome Res 10: 398-400, 2000.
Doerks at al. "Protein annotation: detective work for function prediction", Trends in Genetics 14(6): 248-250, 1998.
Smith et al. "The challenges of genome sequence annotation or 'The devil is in the details'", Nature Biotech 15: 1222-1223, Nov. 1997.
Dumont, Daniel et al. "Vasculotide: A Unique Treatment for Acute Lung Injury, Biellette Therapeutics", York University Biotech Challenge, Executive Summary and presentation, Sep. 21, 2008.
Dumont, Daniel et al. "Vasculotide: A Unique Treatment for Acute Lung Injury, Biellette Therapeutics", pp. 1-10. York University Biotech Challenge, Commercialization Plan, Oct. 19, 2008.
Dumont, Daniel et al. "Vasculotide, An Angiopoietin Peptide-Mimetic for the Treatment of ALI/ARDS Resulting from: Biological & Chemical Warfare; Radiation; Blast-lung; Penetrating Chest Injury; Septic Shock; H1N1 & H5N1; SARS", Canada—U.S. Partners in Biomedical Conference 2009, Embassy of Canada, Washington, DC, Sep. 15, 2009.
Kim, So Ri et al. "Angiopoietin-1 variant, COMP-Ang1 Attenuates Hydrogen Peroxide-Induced Acute Lung Injury", Experimental and Molecular Medicine, vol. 40, No. 3, Jun. 2008, pp. 320-331.
Kumpers, Philipp et al., Systemic Delivery of Recombinant Angiopoietin-1 Ameliorates Multiple-organ Dysfunction Syndrome in Experimental Abdominal Sepsis, Poster, Presented at 8th World Congress on Trauma, Shock, Inflammation and Sepsis, Munich, Germany, Mar. 10, 2010.
Van Der Heijden et al. "The Angiopoietin-Tie2 System as a Therapeutic Target in Sepsis and Acute Lung Injury", Expert Opin. Ther. Targets (2009) 13(1):39-53.
Rubig et al. "The Synthetic Tie2-Agonist Peptide Vasculotide Prevents Intra-Renal Microcirculatory Dysfunction and Improves Survival in Ischemic Acute Kidney Injury", Annual Meeting of the Austrian Society for Intensive Care Medicine and Emergency Medicine (ÖGIAIN) and the German Society for Internal Intensive Care Medicine (DGIIN), Jun. 11-14, 2014, Salzburg, Austria.
York biotech, The Catalyst, vol. 3, Issue 3, Nov. 2008, Newsletter.
Sunnybrook Research Institute, Magazine, Inventing the Future of Health Care, 2008, pp. 52-53.

\* cited by examiner

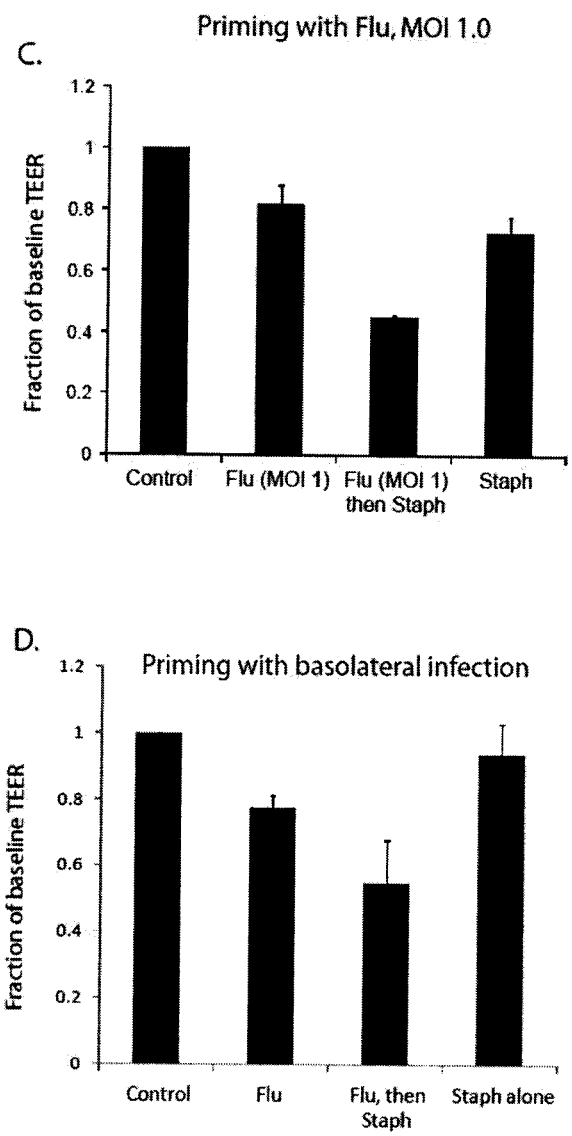
FIGURE 8 CON'T

METHODS, USES AND COMPOSITIONS OF TIE2 AGONISTS

RELATED APPLICATIONS

This application is a national phase entry of PCT/CA2014/000269 filed Mar. 19 2014 (which designates the U.S.) which claims priority from U.S. provisional application No. 61/810,879 filed on Apr. 11, 2013, all of which are incorporated herein by reference in their entirety.

INCORPORATION OF SEQUENCE LISTING

A computer readable form of the Sequence Listing "23632-P43930US01_SequenceListing.txt" (2,343 bytes), submitted via EFS-WEB and created on Sep. 9, 2015, is herein incorporated by reference.

FIELD OF THE DISCLOSURE

The disclosure relates to methods and uses of Tie2 agonists. In particular, the disclosure relates to methods and uses for treating influenza and/or a bacterial superinfection associated with influenza. The disclosure also relates to compositions comprising (a) a Tie2 agonist and (b) an antiviral agent and methods and uses thereof.

BACKGROUND OF THE DISCLOSURE

The human influenza virus exacts a fearsome toll on the economy and on public health (Majury, 2005; Falsey and Walsh, 2006). Despite vaccination programs and antiviral drugs, seasonal influenza alone causes an estimated 4000 Canadian deaths annually (Schanzer et al., 2007) and is the number one infectious cause of death in Ontario (Kuster et al., 2010). Influenza infects the respiratory epithelium and most deaths occur due to pulmonary complications. About 25% of deaths occur as a direct result of the initial viral infection (Louria et al., 1959), while the remainder are attributed to a superimposed bacterial infection (also called a bacterial superinfection), such as pneumonia from *Staphylococcus aureus* (Mohan et al., 2005). In both cases, respiratory deterioration is marked by acute lung injury (Dominguez-Cherit et al., 2009; Louria et al., 1959), a potentially fatal syndrome of pulmonary edema that occurs due to increased permeability of the lung microvasculature (Lee and Slutsky, 2001). Blood vessels in the lung are lined by a continuous layer of endothelium; thus, loss of barrier integrity of the lung microvascular endothelium is a prerequisite for acute lung injury. While antiviral drugs exist, they only partially reduce mortality (McGeer et al., 2007), they must be administered early to be effective, and their use is complicated by the rapid development of resistance. Thus, new therapies for the most severe cases of influenza are desperately needed.

Unlike high pathogenicity avian influenza viruses (e.g. H5N1 avian influenza) (Maines et al., 2008), human influenza strains lack certain basic amino acids in their hemagglutinin molecules; this limits cleavage to trypsin-like proteases that are contained within the respiratory tract. Thus human influenza primarily infects the respiratory epithelium leading to epithelial injury, apoptosis and desquamation (Kuiken and Taubenberger, 2008). In uncomplicated infections, these changes to the airway epithelium are transient and the process of repair is evident within days. However, in primary viral pneumonia, the virus also infects the distal lung, particularly type I pneumocytes and ciliated bronchiolar epithelium, leading to damage to the alveoli including frank alveolar denudement (Kuiken and Taubenberger, 2008); type II pneumocytes and alveolar macrophages can also be infected. In the 1957 flu pandemic, primary viral pneumonias accounted for about 20% of deaths (Kuiken and Taubenberger, 2008). However, the mechanism of lung injury in these cases is not clear, since epithelial apoptosis alone is not sufficient to induce lung leak (Mura et al., 2010).

To date however, a possible effect of influenza on the lung endothelium has been largely overlooked (Teijaro et al., 2011). In vivo, epithelial and endothelial infection, platelet adhesion, and other factors such as systemic cytokines and the release of leukocyte granules may synergize to induce lung injury. To date, however, agents for human influenza targeting the lung endothelium have not been described.

In addition to viral pneumonia, in the 1957 pandemic the remainder of deaths (75%) occurred as a consequence of bacterial superinfection. The classical clinical vignette is of a patient who initially improves after the onset of influenza, only to dramatically deteriorate as early as 2-3 days later (Peltola and McCullers, 2004; Mohan et al., 2005) from bacterial superinfection with Gram-positive organisms like *Staphylococcus aureus*. Autopsy data from the 1918 flu epidemic and data from animal models led to the commonly held hypothesis that the virus caused immunosuppression leading to diminished clearance of bacteria (Speshock et al., 2007). However, antibiotics were not available in 1918 and are not typically used in animal models. Indeed, in the 1957 flu pandemic when antibiotics were readily available, most autopsy lung cultures were negative (Louria et al., 1959; Oseasohn et al., 1959). Thus, the almost universal administration of empiric broad-spectrum antibiotics (McGeer et al., 2007) to patients with severe flu (due to diagnostic uncertainty) makes bacterial replication per se unlikely as the cause of acute lung injury. In support of this notion, in a mouse model of flu and *S. aureus* superinfection, death could not be explained by unrestrained bacterial growth, nor could it be attenuated by depletion of leukocytes (i.e. it was not leukocyte-mediated) (Iverson et al., 2011).

The US Centers for Disease Control and Prevention (CDC) recommend antiviral medications with activity against influenza viruses as important adjunct to influenza vaccines in the control of influenza (see world wide web at cdc.gov/flu/professionals/antivirals/summary-clinicians.htm). Antiviral medications are used in the treatment, as well as prevention, of influenza. FDA-approved antiviral medications include oseltamivir (Tamiflu®) and zanamivir (Relenza®). Clinical benefit is greatest when antivirals are administered early, especially within 48 hours of illness onset and has declining efficacy when given delayed.

Angiopoietins (Ang) 1-4 have all been shown to bind to and activate Tie2 receptor tyrosine kinase activity to differing extents. All the Angs are characterized structurally by an N-terminal super clustering domain (SCD) followed by a coiled-coil domain (CCD) and a C-terminal fibrinogen-like domain (FLD) (Ward and Dumont 2002; Tsigkos et al. 2003). Functional studies have highlighted a role for the SCD and CCD in forming high order homotypic multimers of Ang (Procopio et al. 1999). The specific nature of these multimers is variable and is unique to each Ang family member. Binding specificity of the Angs for the Tie2 receptor has been ascribed to the FLD (Tisgkos et al. 2003; Procopio et al. 1999). Taken together, it is the unique structural attributes of each Ang family member that promotes binding and differential clustering of Tie2. The pleiotropic physiological effects of Angs 1-4 are thought to at least in part be mediated by appropriate and specific clustering of the receptor. For instance, mice engineered to overexpress the CCD of Ang 1, capable of multimerizing with endogenous Ang1 produced in the same cell, caused improper patterning of the coronary vessels (Ward et al. 2004). Furthermore, chimeric forms of Ang 1 engineered to contain the C-terminal FLD and one of several different CCDs differed in their ability to activate the Tie2 receptor (Cho et al. 2004a; Cho et al. 2004b).

The present inventors previously designed peptide mimetics of Angiopoietin that bind to Tie2 and when configured as a dimer or tetramer (the tetramer is known as Vasculotide) result in the clustering of the receptor and its activation (Van Slyke et al. 2009, David et al. 2011, and Kumpers et al. 2011; WO2008/049227).

Activating Tie2 through the tetramerization of high affinity Tie2 binding peptides using the biotin/avidin model (Van Slyke et al. 2009) has established the use of the peptide as an agonist to the Tie2 receptor to promote angiogenesis for applications in diabetic wound healing and other cardiovascular indications. Vasculotide has also been shown to protect against vascular leakage. Studies examining the impact of VT on in vitro endothelium permeability as well as in endotoxemia- and polymicrobial-induced sepsis demonstrated that VT was able to prevent and/or reverse endothelial permeability induced by these treatments. Moreover VT was able to prevent the breakdown of EC:EC interactions in vitro further illustrating its ability to inhibit vascular permeability (David et al. 2011).

SUMMARY OF THE DISCLOSURE

The present inventors have shown that that administration of a multimeric form of a Tie2 binding peptide called "Vasculotide" is able to increase survival in a mouse model of primary viral pneumonia and acute lung injury due to influenza viral infection, and to increase survival when co-administered with an antiviral drug. The increase in survival persists even when Vasculotide is given in a delayed fashion (i.e. after the onset of infection with influenza). The inventors have also shown that low-dose infection with influenza predisposes the lung endothelium to increased leak upon subsequent exposure to bacteria, a phenomenon known as priming and that Vasculotide is able to abrogate this priming-induced leak.

Accordingly, the present disclosure provides a method of treating an animal or cell infected with influenza comprising administering a Tie2 agonist. The disclosure also provides use of a Tie2 agonist for treating an animal or cell infected with influenza. Also provided is use of a Tie2 agonist in the preparation of a medicament for treating an animal or cell infected with influenza. Further provided is a Tie2 agonist for use in treating an animal or cell infected with influenza.

The present disclosure also provides a method of increasing survival and/or decreasing mortality in an animal infected with influenza comprising administering a Tie2 agonist. The disclosure also provides use of a Tie2 agonist for increasing survival and/or decreasing mortality in an animal infected with influenza. Also provided is use of a Tie2 agonist in the preparation of a medicament for increasing survival and/or decreasing mortality in an animal infected with influenza. Further provided is a Tie2 agonist for use in increasing survival and/or decreasing mortality in an animal infected with influenza.

The present disclosure also provides a method of decreasing lung endothelial leak in an animal or cell infected with influenza comprising administering a Tie2 agonist. The disclosure also provides use of a Tie2 agonist for decreasing lung endothelial leak in an animal or cell infected with influenza. Also provided is use of a Tie2 agonist in the preparation of a medicament for decreasing lung endothelial leak in an animal or cell infected with influenza. Further provided is a Tie2 agonist for use in decreasing lung endothelial leak in an animal or cell infected with influenza.

The present disclosure also provides a method of increasing arterial oxygen saturation in an animal or cell infected with influenza comprising administering a Tie2 agonist. The disclosure also provides use of a Tie2 agonist for increasing arterial oxygen saturation in an animal or cell infected with influenza. Also provided is use of a Tie2 agonist in the preparation of a medicament for increasing arterial oxygen saturation in an animal or cell infected with influenza. Further provided is a Tie2 agonist for use in increasing arterial oxygen saturation in an animal or cell infected with influenza.

The present disclosure also provides a method of treating a bacterial superinfection associated with influenza in an animal or cell in need thereof comprising administering a Tie2 agonist. The disclosure also provides use of a Tie2 agonist for treating a bacterial superinfection associated with influenza in an animal or cell in need thereof. Also provided is use of a Tie2 agonist in the preparation of a medicament for treating a bacterial superinfection associated with influenza in an animal or cell in need thereof. Further provided is a Tie2 agonist for use in treating a bacterial superinfection associated with influenza in an animal or cell in need thereof.

The present disclosure also provides a method of increasing survival and/or decreasing mortality in an animal with a bacterial superinfection associated with influenza comprising administering a Tie2 agonist. The disclosure also provides use of a Tie2 agonist for increasing survival and/or decreasing mortality in an animal with a bacterial superinfection associated with influenza. Also provided is use of a Tie2 agonist in the preparation of a medicament for increasing survival and/or decreasing mortality in an animal with a bacterial superinfection associated with influenza. Further provided is a Tie2 agonist for use in increasing survival and/or decreasing mortality in an animal with a bacterial superinfection associated with influenza.

The present disclosure also provides a method of decreasing lung endothelial leak in an animal or cell with a bacterial superinfection associated with influenza comprising administering a Tie2 agonist. The disclosure also provides use of a Tie2 agonist for decreasing lung endothelial leak in an animal or cell with a bacterial superinfection associated with influenza. Also provided is use of a Tie2 agonist in the preparation of a medicament for decreasing lung endothelial leak in an animal or cell with a bacterial superinfection associated with influenza. Further provided is a Tie2 agonist for use in decreasing lung endothelial leak in an animal or cell with a bacterial superinfection associated with influenza.

The Tie2 agonist may be administered in any suitable manner, including without limitation, topically, systemically, orally, intranasally or by inhalation.

In an embodiment, the Tie2 agonist is used or administered about or at least 24 hours post-infection. In another embodiment, the Tie2 agonist is used or administered about or at least 48 hours post-infection. In yet another embodiment, the Tie2 agonist is used or administered about or at least 72 hours post-infection.

The present disclosure also provides a method of treating an animal or cell infected with influenza comprising administering (a) a Tie2 agonist and (b) an antiviral agent. The disclosure also provides use of (a) a Tie2 agonist and (b) an antiviral agent for treating an animal or cell infected with influenza. Also provided is use of (a) a Tie2 agonist and (b) an antiviral agent in the preparation of a medicament for treating an animal or cell infected with influenza. Further provided is (a) a Tie2 agonist and (b) an antiviral agent for use in treating an animal or cell infected with influenza.

The present disclosure also provides a method of increasing survival and/or decreasing mortality in an animal infected with influenza comprising administering (a) a Tie2 agonist and (b) an antiviral agent. The disclosure also provides use of (a) a Tie2 agonist and (b) an antiviral agent for increasing survival and/or decreasing mortality in an animal infected with influenza. Also provided is use of (a) a Tie2 agonist and (b) an antiviral agent in the preparation of a medicament for increasing survival and/or decreasing mortality in an animal infected with influenza. Further provided is (a) a Tie2 agonist and (b) an antiviral agent for use in increasing survival and/or decreasing mortality in an animal infected with influenza.

The present disclosure also provides a method of decreasing lung endothelial leak in an animal or cell infected with influenza comprising administering (a) a Tie2 agonist and (b) an antiviral agent. The disclosure also provides use of (a) a Tie2 agonist and (b) an antiviral agent for decreasing lung endothelial leak in an animal infected with influenza. Also provided is use of (a) a Tie2 agonist and (b) an antiviral agent in the preparation of a medicament for decreasing lung endothelial leak in an animal infected with influenza. Further provided is (a) a Tie2 agonist and (b) an antiviral agent for use in decreasing lung endothelial leak in an animal infected with influenza.

The Tie2 agonist may be administered in any suitable manner, including without limitation, topically, systemically, orally, intranasally or by inhalation. The antiviral agent may also be administered in any suitable manner, including without limitation, topically, systemically, orally, intranasally or by inhalation.

The Tie2 agonist and the antiviral agent may be administered concurrently (at the same time). The Tie2 agonist and the antiviral agent may also be administered sequentially. The Tie2 agonist may be administered before the antiviral agent or the antiviral agent may be administered before the Tie2 agonist. In an embodiment, the Tie2 agonist is used or administered about or at least 24 hours after the anti-viral agent. In another embodiment, the Tie2 agonist is used or administered about or at least 48 hours after the anti-viral agent. In yet another embodiment, the Tie2 agonist is used or administered about or at least 72 hours after the anti-viral agent.

In one embodiment, the influenza is human influenza.

The present disclosure also provides a composition comprising (a) a Tie2 agonist and (b) an antiviral agent. Optionally, the composition further comprises a pharmaceutically acceptable carrier.

The present disclosure also provides a kit comprising (a) a Tie2 agonist and (b) an antiviral agent. In one embodiment, the kit further comprises instructions for use for treating influenza in an animal or cell in need thereof.

In one embodiment, the antiviral agent is an inhibitor of an influenza virus. In another embodiment, the antiviral agent is amantadine, rimantadine, zanamivir, peramivir, viramidine, ribavirin or oseltamivir (also known as Tamiflu®). In another embodiment, the antiviral agent is oseltamivir (Tamiflu®).

In an embodiment, the Tie2 agonist is a binding and/or activating agent. In an embodiment, the Tie2 agonist binds the Tie2 receptor directly and thus is a Tie2 binding and activating agent. In another embodiment, the Tie2 agonist activates the Tie2 receptor indirectly and thus is a Tie2 activating agent.

In one embodiment, the Tie2 agonist comprises an angiopoietin-1 or a nucleic acid encoding angiopoietin-1. In another embodiment, the Tie2 agonist comprises an inhibitor of angiopoietin-2, such as a blocking antibody or peptibody against angiopoietin-2 or an antisense nucleic acid against angiopoietin-2.

In another embodiment, the Tie2 agonist comprises a multimeric form of a Tie2 binding peptide monomer.

The multimeric form can be, for example, a dimer, tetramer, or a multimeric form that comprises six, eight, ten or twelve units of the monomer. In another embodiment, the multimeric form comprises an odd number of units, such as three, five, seven, nine or eleven units.

In yet another embodiment, the Tie2 binding peptide monomer comprises a structure: A-B-C, wherein A comprises a Tie2 binding peptide, B comprises a spacer and C comprises a multimerizing group, wherein C has affinity for D, a multimer agent comprising multiple binding sites for C. For example, the multimer agent D can have four binding sites for the multimerizing group C such that a tetramer is formed when four Tie2 binding peptide monomers, A-B-C, interact with the multimer agent D. In an embodiment, C comprises a biotin group and D comprises an agent selected from the group consisting of avidin, streptavidin and neutravidin. In yet another embodiment, B comprises polyethylene glycol (PEG).

In a further embodiment, the Tie2 binding peptide monomer comprises a structure: A-B, wherein A comprises a Tie2 binding peptide and B comprises a common spacer, wherein the multimeric form is created by covalent linkage of multiple Tie2 binding peptides via the common spacer B. In an embodiment, B comprises polyethylene glycol (PEG).

Tie2 binding peptides for use in the monomers include, but are not limited to, a T7 peptide as shown in SEQ ID NOs: 1 or 2, a GA3 peptide as shown in SEQ ID NOs: 3 or 4, a T6 peptide as shown in SEQ ID NOs: 7 or 8 or a T8 peptide as shown in SEQ ID NOs: 5 or 6. In an alternative embodiment, the Tie2 binding peptide is a T4 peptide as shown in SEQ ID NOs: 9 or 10.

In another embodiment, the multimeric form is a dimer, comprising: (a) a first peptide chain; (b) a second peptide chain; and (c) a linking moiety connecting said first and second peptide chains, wherein said peptide dimer binds to and activates the Tie2 receptor. In one embodiment, the first peptide chain is a T7 peptide (SEQ ID NOs: 1 or 2) and/or the second peptide chain is a T7 peptide (SEQ ID NOs: 1 or 2). Optionally, the linking moiety comprises one or more water-soluble polymers covalently bound to the first peptide chain and the second peptide chain. The one or more water-soluble polymers may be linear polymers. In one embodiment, the water-soluble polymer is a polyethylene glycol (PEG), optionally having a molecular weight in the range of about 3,000 Daltons to 50,000 Daltons or about 3,000 Daltons to 20,000 Daltons. In various embodiments, the PEG has a molecular weight of about 3,000, about 3,400, about 5,000, about 10,000, about 15,000, about 20,000, about 25,000, about 30,000 or about 40,000 Daltons.

In yet another embodiment, the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie2 receptor. Optionally, the first, second, third and fourth peptide chains are T7 peptides (SEQ ID NOs: 1 or 2). The linking moiety may comprise one or more water-soluble polymers covalently bound to the first, second, third and fourth peptide chains. In one embodiment, the water-soluble polymer is a branched chain water-soluble polymer, such as PEG. The branched PEG may have a molecular weight in a range of about 3,000 Daltons to about 50,000 Daltons or about 3,000 Daltons to about 20,000 Daltons. In various embodiments, the PEG has a molecular weight of about 3,000, about 3,400, about 5,000, about 10,000, about 15,000, about 20,000, about 25,000, about 30,000 or about 40,000 Daltons.

The multimeric forms described herein exhibit Tie2 agonist activity. For example, the multimeric form stimulates Tie2 phosphorylation or stimulates phosphorylation of MAPK, AKT and eNOS.

In a particular embodiment, the multimeric form is a tetramer and the Tie2 binding peptide monomer comprises a structure: A-B-C, wherein:

A comprises a Tie2 binding peptide selected from a T7 peptide (SEQ ID NOs: 1 or 2) and a GA3 peptide (SEQ ID NOs: 3 or 4);

B comprises a polyethylene glycol spacer; and

C comprises a biotin group, wherein four copies of A-B-C are associated with a tetramer agent, D, to create the tetramer form, the tetramer agent, D, being selected from the group consisting of avidin, streptavidin and neutravidin.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

Figure 1:
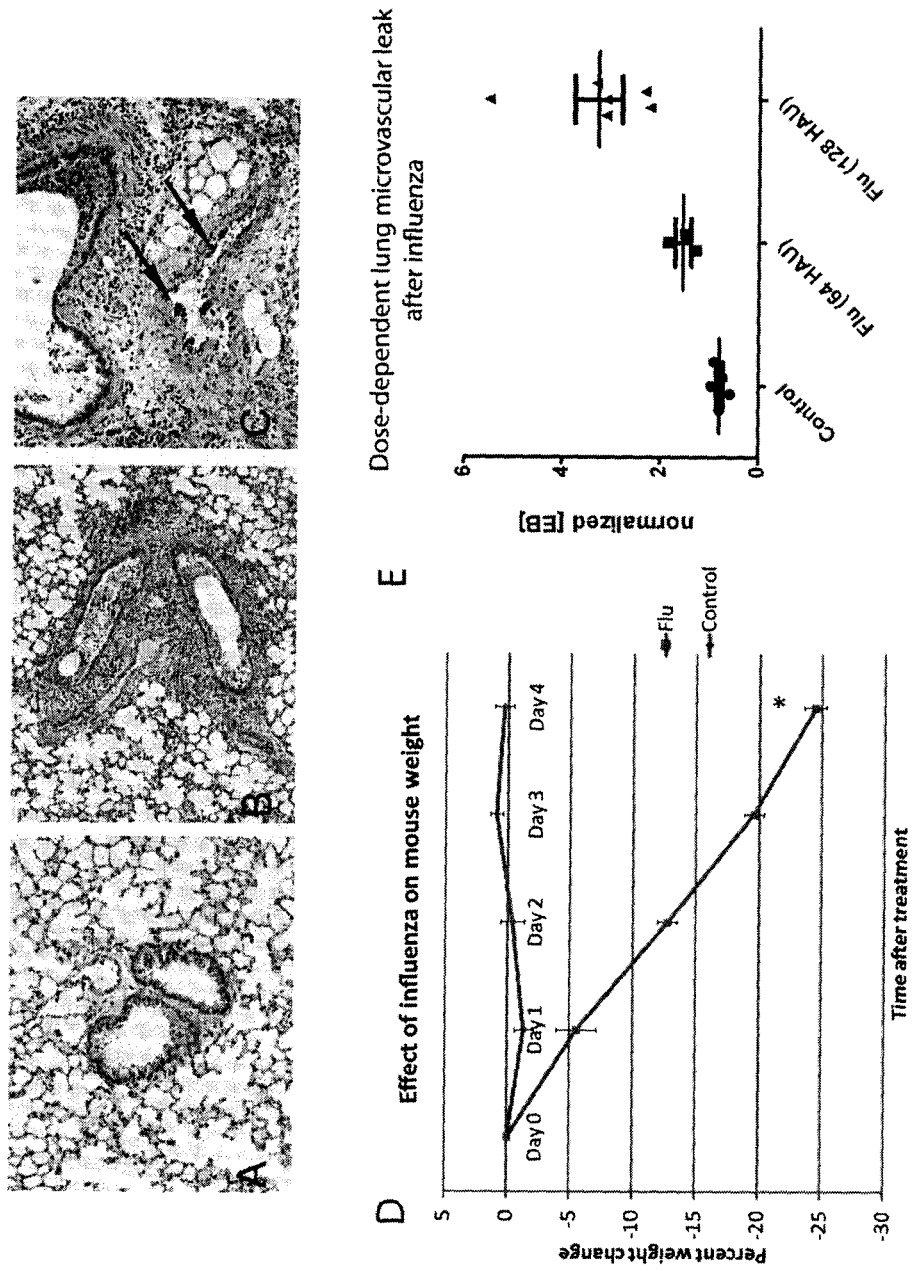
FIG. 1 shows (A) histology (H&E) of an uninfected lung with a normal bronchovascular bundle and surrounding alveoli; (B) an infected lung (3 days post-infection) showing bronchiolitis, peribronchiolitis with focal interstitial inflammation and congested alveolar septae; (C) a higher power view of the infected lung of (B) showing marked margination of inflammatory cells and reactive change of endothelium (arrows), as well as necrotic debris within the bronchiolar lumen; (D) the effect of influenza on mouse weight. C57Bl/6 mice were inoculated intranasally with influenza X31 (128 hemagglutinin units (HAU)) or saline and weighed daily; and (E) lung microvascular leak is dose-dependent. Mice were infected intranasally with 64 or 128 HAU of influenza and lung vascular leak as measured by Evans Blue dye leak on day 4 ($p<0.01$ by ANOVA).

The present inventors have shown that administration of a multimeric form of a Tie2 binding peptide called "Vasculotide" is able to increase survival in a mouse model of primary viral pneumonia and acute lung injury, and to increase survival when co-administered with an antiviral drug. The inventors have also shown that low-dose infection with influenza predisposes the lung endothelium to increased leak upon subsequent exposure to bacteria, a phenomenon known as priming, and that Vasculotide is able to abrogate this priming-induced leak.

Definitions:

As used herein, the term "Vasculotide" refers to a peptide tetramer that binds to and activates the Tie2 receptor. Vasculotide comprises: (a) a first peptide chain; (b) a second peptide chain; (c) a third peptide chain; (d) a fourth peptide chain; and (e) a linking moiety connecting said first, second, third and fourth peptide chains, wherein the first, second, third and fourth peptide chains are T7 peptides and the linking moiety is 10,000 Dalton PEG. Further details about the preparation of Vasculotide is found in the Examples. In another embodiment, mercaptopropionic acid replaces the cysteine.

As used herein, the term "Tie2" refers to a receptor protein tyrosine kinase that is expressed almost exclusively on endothelial and progenitor cells and that is also known in the art as TEK, p140 TEK, CD202B and VMCM. The term "Tie2" is intended to encompass the receptor from any species that expresses this receptor. In one embodiment, Tie2 is a human Tie2. The mRNA and protein sequences of human Tie2 are set forth at GenBank Accession Nos. NM_000459 and NP_000450, respectively.

As used herein, the term "angiopoietin" is intended to refer to any one of a family of protein growth factors known to be ligands for Tie2, including angiopoietin 1 (or Ang 1), angiopoietin 2 (or Ang 2), angiopoietin 3 (or Ang 3) and angiopoietin 4 (or Ang 4). The term "angiopoietin" is intended to encompass the growth factor from any species that expresses the growth factor, optionally human angiopoietin family members. The mRNA and protein sequences of human Ang 1 are set forth at GenBank Accession Nos. NM_001146 and NP_001137, respectively. The mRNA and protein sequences of human Ang 2 are set forth at GenBank Accession Nos. NM_001147 and NP_001138, respectively. The mRNA and protein sequences of human Ang 4 are set forth at GenBank Accession Nos. NM_015985 and NP_057069, respectively.

As used herein, the term "MAPK" is intended to refer to mitogen activated protein kinase, also known as ERK or extracellular signal-regulated kinase, an intracellular kinase that is phosphorylated upon activation of Tie2. The term "MAPK" is intended to encompass the kinase from any species that expresses the kinase, optionally human MAPK. The mRNA and protein sequences of human MAPK are set forth at GenBank Accession Nos. NM_002736 and NP_002745, respectively.

As used herein, the term "AKT" is intended to refer to a protein kinase also known as v-akt murine thymoma viral oncogene homolog, an intracellular kinase that is phosphorylated upon activation of Tie2. The term "AKT" is intended to encompass the kinase from any species that expresses the kinase, optionally human AKT. The mRNA and protein sequences of human AKT are set forth at GenBank Accession Nos. NM_001014431 and NP_001014431, respectively.

As used herein, the term "eNOS" is intended to refer to endothelial cell nitric oxide synthetase, also known as NOS 3, NOS III or ECNOS, an intracellular enzyme that is phosphorylated upon activation of Tie2. The term "eNOS" is intended to encompass the enzyme from any species that expresses the enzyme, optionally human eNOS. The mRNA and protein sequences of human eNOS are set forth at GenBank Accession Nos. NM_000603 and NP_000594, respectively.

As used herein, the term "Tie2 binding peptide" is intended to encompass peptides at least four amino acids in length and optionally no more than 100 amino acids in length that have binding affinity for Tie2. Furthermore, the term "Tie2 binding peptide" is intended to encompass peptides comprised in whole or in part of L-amino acids, peptides comprised in whole or in part of D-amino acids and peptides comprised of both L- and D-amino acids. Still further, the term "Tie2 binding peptide" is intended to encompass peptides comprised in whole or in part of the 20 naturally-occurring amino acid residues, peptides comprised in whole or in part of non-naturally-occurring amino acid residues and peptide comprised of both naturally-occurring and non-naturally-occurring amino acid residues.

As used herein, the term "Tie2 binding peptide monomer" is intended to refer to a single unit of a Tie2 binding peptide compound. The Tie2 binding peptide compound, or monomer, comprises the Tie2 binding peptide, and may comprise other chemical moieties (e.g., spacers, multimerizing groups and the like), but the Tie2 binding peptide monomer comprises only one copy (or unit) of the Tie2 binding peptide and thus has a single valency for the Tie2 receptor.

As used herein, the term "peptide" can also refer to proteins.

As used herein, the term "multimeric form" of a Tie2 binding peptide monomer is intended to refer to forms that contain more than one unit of the Tie2 binding peptide monomer such that the multimeric form (e.g., dimer, tetramer and the like) comprises more than one copy (or unit) of the Tie2 binding peptide and thus has multivalency for the Tie2 receptor. In a particular embodiment, the multimeric form is a tetramer. Multimeric forms of Tie2 binding peptides have been previously described in WO 2008/049227, incorporated herein by reference in its entirety.

As used herein, the term "high affinity", as used with respect to binding of a Tie2 binding peptide to the Tie2 receptor, is intended to mean binding of the peptide to the receptor with $K_d$ of about $10^{-3}$ M or less, $10^{-4}$ M or less, or $10^{-5}$ M or less.

As used herein, the term "Tie2 agonist" is intended to refer to an agent that effects biology consistent with Tie2 receptor signaling, for example, an agent that is capable of stimulating, enhancing, increasing or upregulating Tie2 receptor activity and/or stability, as measured by any method, technique, signal, detector or indicator that is known in the art to be indicative of Tie2 receptor biology. Non-limiting examples of indicators of Tie2 receptor activity include phosphorylation of human Tie2 at amino acid residue Y897, Y992, Y1048, Y1102, Y1108 or Y1113, or at amino acid Y1100, Y1106, or Y1106, 1111 of mouse Tie2, or phosphorylation of one or more of MAPK, AKT and eNOS.

Methods and Uses

The present inventors have shown that administration of a multimeric form of a Tie2 binding peptide, called Vasculotide, is able to increase survival in a mouse model of primary viral pneumonia and acute lung injury.

Accordingly, the present disclosure provides a method of treating an animal or cell infected with influenza comprising administering a Tie2 agonist. The disclosure also provides use of a Tie2 agonist for treating an animal or cell infected with influenza. Also provided is use of a Tie2 agonist in the preparation of a medicament for treating an animal or cell infected with influenza. Further provided is a Tie2 agonist for use in treating an animal or cell infected with influenza.

The present disclosure also provides a method of increasing survival and/or decreasing mortality in an animal or cell infected with influenza comprising administering a Tie2 agonist. The disclosure also provides use of a Tie2 agonist for increasing survival and/or decreasing mortality in an animal or cell infected with influenza. Also provided is use of a Tie2 agonist in the preparation of a medicament for increasing survival and/or decreasing mortality in an animal or cell infected with influenza. Further provided is a Tie2 agonist for use in increasing survival and/or decreasing mortality in an animal or cell infected with influenza.

The present inventors have also shown that influenza induces lung endothelial leak, in contrast to the traditional scientific consensus in which influenza virus affects only the epithelium, and that this is a determinant of mortality from lung infections. The inventors have further shown that Vasculotide reduces lung microvascular leak from influenza or complications arising from influenza.

Accordingly, the present disclosure also provides a method of decreasing lung endothelial leak in an animal or cell infected with influenza comprising administering a Tie2 agonist. The disclosure also provides use of a Tie2 agonist for decreasing endothelial leak in an animal or cell infected with influenza. Also provided is use of a Tie2 agonist in the preparation of a medicament for decreasing endothelial leak in an animal or cell infected with influenza. Further provided is a Tie2 agonist for use in decreasing endothelial leak in an animal or cell infected with influenza.

As used herein, the term "influenza" refers to an infectious disease caused by RNA viruses of the family Orthomyxoviridae. The term influenza also refers to primary viral pneumonia. In one embodiment, influenza is a disease caused by a human influenza virus. Human influenza viruses can be distinguished from avian influenza viruses (for example, H5N1 avian influenza) by the lack of certain basic amino acids in their hemagglutinin molecules; this limits cleavage to trypsin-like proteases that are contained within the respiratory tract. Thus, human influenza primarily infects the respiratory epithelium leading to epithelial injury, apoptosis and desquamation (Kuiken and Taubenberger, 2008). In contrast, avian influenza viruses can replicate outside of the respiratory tract and target endothelial cells. Human influenza viruses can also be distinguished from avian influenza viruses on the basis that human influenza viruses can spread from human to human but avian influenza viruses cannot spread from human to human. Non-limiting examples of human influenza viruses include the following: H1N1, H3N2, H2N2, and H1N2.

As used herein, the term "lung endothelial leak" refers to a loss of barrier integrity or increased permeability of the lung microvascular endothelium. The term "decreasing lung endothelial leak" refers to a decrease of lung endothelial leak of at least 5, 10, 15, 25, 50, 75 or 100% compared to a control that is not treated by the methods and uses described herein. In one embodiment, lung endothelial leak is measured by transendothelial electrical resistance (TEER) or fluorescence of a fluorescein-tagged compound such as dextran. The term "decreasing lung endothelial leak" also refers to an increase in permeability of lung microvascular endothelium of at least 5, 10, 15, 25, 50, 75 or 100% compared to a control that is not treated by the methods and uses described herein.

The present inventors have also shown that low-dose infection with influenza predisposes the lung endothelium to increased leak upon subsequent exposure to bacteria, a phenomenon known as priming and that Vasculotide is able to abrogate this priming-induced leak.

Accordingly, the present disclosure also provides a method of treating a bacterial superinfection associated with influenza in an animal or cell in need thereof comprising administering a Tie2 agonist. The disclosure also provides use of a Tie2 agonist for treating a bacterial superinfection associated with influenza in an animal or cell in need thereof. Also provided is use of a Tie2 agonist in the preparation of a medicament for treating a bacterial superinfection associated with influenza in an animal or cell in need thereof. Further provided is a Tie2 agonist for use in treating a bacterial superinfection associated with influenza in an animal or cell in need thereof.

The present disclosure also provides a method of increasing survival and/or decreasing mortality in an animal or cell with a bacterial superinfection associated with influenza comprising administering a Tie2 agonist. The disclosure also provides use of a Tie2 agonist for increasing survival and/or decreasing mortality in an animal or cell with a bacterial superinfection associated with influenza. Also provided is use of a Tie2 agonist in the preparation of a medicament for increasing survival and/or decreasing mortality in an animal or cell with a bacterial superinfection associated with influenza. Further provided is a Tie2 agonist for use in increasing survival and/or decreasing mortality in an animal or cell with a bacterial superinfection associated with influenza.

The present disclosure also provides a method of decreasing lung endothelial leak in an animal or cell with a bacterial superinfection associated with influenza comprising administering a Tie2 agonist. The disclosure also provides use of a Tie2 agonist for decreasing lung endothelial leak in an animal or cell with a bacterial superinfection associated with influenza. Also provided is use of a Tie2 agonist in the preparation of a medicament for decreasing lung endothelial leak in an animal or cell with a bacterial superinfection associated with influenza. Further provided is a Tie2 agonist for use in decreasing lung endothelial leak in an animal or cell with a bacterial superinfection associated with influenza.

As used herein, the term "bacterial superinfection" refers to a bacterial infection that arises secondary to, or typically following, a primary influenza infection, including a low-dose influenza infection. A bacterial superinfection can also be defined as a pneumonia that occurs simultaneous with or following influenza infection. In one embodiment, the bacterium responsible for the bacterial superinfection is a Gram-positive bacterium such as *Staphylococcus aureus* (*S. aureus*) or *Staphylococcus pneumonia* (*S. pneumonia*). Without being bound by theory, it is believed that influenza primes the lung endothelium, making it more susceptible to leak when a secondary bacterial infection occurs. As a result, bacterial superinfections can cause severe lung injury after otherwise routine infections with influenza.

As used herein, the expression "a bacterial superinfection associated with influenza" refers in one embodiment to a bacterial superinfection that occurs at the same time, or simultaneously with, an influenza infection. In another embodiment, the expression "a bacterial superinfection associated with influenza" refers to a bacterial superinfection that occurs subsequent to, or following, an influenza infection.

Current treatment with antiviral agents is not as effective as time passes between initial onset of infection and treatment, which is problematic as patients do not always present for treatment immediately after symptoms arise. In contrast to the declining efficacy of antiviral treatment, the present inventors have demonstrated that Vasculotide is effective even if given in a delayed fashion.

Accordingly, in an embodiment, the Tie2 agonist is used or administered about or at least 24 hours post-infection. In another embodiment, the Tie2 agonist is used or administered about or at least 48 hours post-infection. In yet another embodiment, the Tie2 agonist is used or administered about or at least 72 hours post-infection.

The present inventors have also shown that treatment with Vasculotide does not reduce the efficacy of antiviral treatment and administration of a Tie2 agonist, for example, Vasculotide, in combination with an antiviral drug is able to increase survival in a mouse model of primary viral pneumonia and acute lung injury due to influenza. Accordingly, the present disclosure also provides a method of treating an animal or cell infected with influenza comprising administering (a) a Tie2 agonist and (b) an antiviral agent to the animal or cell in need thereof. The disclosure also provides use of (a) a Tie2 agonist and (b) an antiviral agent for treating an animal or cell infected with influenza. Also provided is use of (a) a Tie2 agonist and (b) an antiviral agent in the preparation of a medicament for treating an animal or cell infected with influenza. Further provided is (a) a Tie2 agonist and (b) an antiviral agent for use in treating an animal or cell infected with influenza.

The present disclosure also provides a method of increasing survival and/or decreasing mortality in an animal or cell infected with influenza comprising administering (a) a Tie2 agonist and (b) an antiviral agent. The disclosure also provides use of (a) a Tie2 agonist and (b) an antiviral agent for increasing survival and/or decreasing mortality in an animal or cell infected with influenza. Also provided is use of (a) a Tie2 agonist and (b) an antiviral agent in the preparation of a medicament for increasing survival and/or decreasing mortality in an animal or cell infected with influenza. Further provided is (a) a Tie2 agonist and (b) an antiviral agent for use in increasing survival and/or decreasing mortality in an animal or cell infected with influenza.

The present disclosure also provides a method of decreasing lung endothelial leak in an animal or cell infected with influenza comprising administering (a) a Tie2 agonist and (b) an antiviral agent. The disclosure also provides use of (a) a Tie2 agonist and (b) an antiviral agent for decreasing lung endothelial leak in an animal or cell infected with influenza. Also provided is use of (a) a Tie2 agonist and (b) an antiviral agent in the preparation of a medicament for decreasing lung endothelial leak in an animal or cell infected with influenza. Further provided is (a) a Tie2 agonist and (b) an antiviral agent for use in decreasing lung endothelial leak in an animal or cell infected with influenza.

The term "antiviral agent" as used herein refers to a drug used to treat viral infections such as infections with influenza viruses. In one embodiment, an antiviral agent is an agent that suppresses the ability of a virus to reproduce. Examples of antiviral agents include, but are not limited to, amantadine, rimantadine, zanamivir, peramivir, viramidine, ribavirin and oseltamivir (also known as Tamiflu®).

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. As used herein, the term "treatment or treating" also includes preventing or retarding a bacterial superinfection secondary to viral infection with influenza. Examples of beneficial results of flu treatment include increasing survival, decreasing mortality, decreasing lung endothelial leak, decreasing weight loss and/or preventing hypothermia and improving arterial oxygenation.

The term "increasing survival" as used herein means increasing the length of time an animal survives following infection with influenza and/or bacterial superinfection associated with influenza. In one embodiment, the term "increasing survival" refers to at least a 5, 10, 25, 50, 75, 100, 200% increase in the length of time an animal survives following infection with influenza compared to an animal that is not treated with the methods and uses described herein.

The term "decreasing mortality" as used herein means decreasing the mortality rate of an animal or cell with influenza and/or bacterial superinfection associated with influenza when compared to an animal that is not treated with the methods and uses described herein. In one embodiment, the mortality rate is decreased by at least 5, 10, 15, 20, 25, 30, 35, 40, 45, 50, 55, 60, 65, 70, 75, 80, 85, 90, 95% when compared to an animal that is not treated with the methods and uses described herein.

The term "administering" includes the administration of the agents described herein to an animal or to a cell in vitro or in vivo.

The term "animal" as used herein includes all members of the animal kingdom including humans.

The term "cell" includes a single cell as well as a plurality or population of cells. Administering to a cell includes administering in vitro (or ex vivo) as well as in vivo.

The Tie2 agonist may be administered by any suitable method, including topically, systemically, orally, intranasally or by inhalation.

The antiviral agent may also be administered in any suitable manner, including without limitation, topically, systemically, orally, intranasally or by inhalation.

The Tie2 agonist and the antiviral agent may be administered concurrently (at the same time). In another embodiment, the Tie2 agonist and the antiviral agent may be administered sequentially. The Tie2 agonist may be administered before the antiviral agent or the antiviral agent may be administered before the Tie2 agonist. In an embodiment, the Tie2 agonist is used or administered about or at least 24 hours after the anti-viral agent. In another embodiment, the Tie2 agonist is used or administered about or at least 48 hours after the anti-viral agent. In yet another embodiment, the Tie2 agonist is used or administered about or at least 72 hours after the anti-viral agent.

Administration of an "effective amount" of the agents described herein is defined as an amount effective, at dosages and for periods of time necessary to achieve the desired result. The effective amount of the Tie2 binding and/or activating agent may vary according to factors such as the disease state, age, sex, and weight of the animal. The effective amount of the antiviral agent may also vary according to factors such as the disease state, age, sex, and weight of the animal.

Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or topical application or ex vivo in culture) will also impact the dosage regime.

The methods and uses described herein include administration or use of the Tie2 agonist alone or as part of a pharmaceutical composition comprising the Tie2 agonist.

In one embodiment, the pharmaceutical composition comprising the Tie2 agonist for use in the methods and uses herein further comprises an antiviral agent. Optionally, the composition further comprises a pharmaceutically acceptable carrier.

Such pharmaceutical compositions can be for intralesional, intravenous, topical, rectal, parenteral, local, inhalant, intranasal or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999.

On this basis, the pharmaceutical compositions for use in the methods and/or uses described herein include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as corticosteroids and immune modulators.

Compositions Comprising (a) a Tie2 Agonist and (b) an Antiviral Agent

The present inventors demonstrated that the administration of the Tie2 agonist, Vasculotide, in combination with an antiviral drug does not reduce the efficacy of the antiviral drug and is able to increase survival in a mouse model of primary viral pneumonia and acute lung injury due to influenza.

Accordingly, the disclosure provides a composition comprising (a) a Tie2 agonist as described herein and (b) an antiviral agent. Optionally, the composition further comprises a pharmaceutically acceptable carrier.

The antiviral agent is any agent used to treat viral infections such as infections with influenza viruses. In one embodiment, an antiviral agent is an agent that suppresses the ability of an influenza virus to reproduce. Examples of antiviral agents include, but are not limited to, amantadine, rimantadine, zanamivir, peramivir, viramidine, ribavirin and oseltamivir (also known as Tamiflu®).

Such pharmaceutical compositions can be for intralesional, intravenous, topical, rectal, parenteral, local, inhalant, intranasal or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003 —20$^{th}$ Edition) and in The United States Pharmacopeia: The National Formulary (USP 24 NF19) published in 1999.

On this basis, the pharmaceutical compositions described herein include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as corticosteroids and immune modulators.

The disclosure also provides a kit comprising (a) a Tie2 agonist as described herein and (b) an antiviral agent as described herein.

In one embodiment, the kit further comprises a container. In another embodiment, the kit contains instructions for use of the kit for treating influenza in an animal or cell in need thereof and/or for increasing survival and/or decreasing mortality in an animal with influenza. In other embodiments, the kit contains instructions for use of the kit for treating a bacterial superinfection associated with influenza in an animal or cell in need thereof. In further embodiments, the kit provides instructions for use of the kit for decreasing lung endothelial leak in an animal with influenza.

The Tie2 agonist and the antiviral agent of the kit are optionally for use concurrently or sequentially. The Tie2 agonist may be for use before the antiviral agent or the antiviral agent may be for use before the Tie2 agonist.

Tie2 Agonists for Use in the Methods, Uses, Compositions and Kits Described Herein Angiopoietin-1

The Tie2 agonist can either bind and activate the Tie2 receptor, i.e. act directly, or it can activate the Tie2 receptor indirectly. As such, another term of Tie2 agonist is Tie2 binding and/or activating agent.

In one embodiment, the Tie2 agonist comprises an angiopoietin-1 protein or a variant thereof. In one embodiment, the angiopoietin-1 protein comprises the amino acid sequence as shown in NP_00137 or a variant thereof.

In another embodiment, the Tie2 agonist comprises a nucleic acid encoding an angiopoietin-1 protein or variant thereof. In one embodiment, the angiopoietin-1 nucleic acid molecule comprises the amino acid sequence as shown in NM_00146 or a variant thereof. In another embodiment, the Tie2 agonist comprises the receptor binding domain of angiopoietin-1.

The term "nucleic acid" as used herein refers to a sequence of nucleotide or nucleoside monomers consisting of naturally occurring bases, sugars and intersugar (backbone) linkages. The nucleic acid sequences may be ribonucleic (RNA) or deoxyribonucleic acids (DNA).

The term "variant" as used herein includes modifications, substitutions, additions, derivatives, analogs, fragments, chimeric versions or chemical equivalents of the angiopoietin amino acid sequences that perform substantially the same function as the angiopoietin peptides disclosed herein in substantially the same way. For instance, the variants of the angiopoietin peptides would have the same function of being able to bind to and activate Tie2 when presented as a multimeric form.

Variants also include peptides with amino acid sequences that are substantially or essentially identical to the angiopoietin sequences.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "angiopoietin-1 fragment" as used herein means a portion of the angiopoietin-1 peptide that contains at least 10%, 20%, 30%, 40%, 50%, 60%, 70%, 80%, 90%, 95%, or more of the entire length of the angiopoietin-1 polypeptide that is able to bind and/or activate Tie2 when presented as a multimeric form.

The term "homolog" means those amino acid or nucleic acid sequences which have slight or inconsequential sequence variations from angiopoietin-1, i.e., the sequences function in substantially the same manner. The variations may be attributable to local mutations or structural modifications, Sequences having substantial homology include nucleic acid sequences having at least 65%, at least 85%, or 90-95% identity with angiopoietin-1 sequences. Sequence identity can be calculated according to methods known in the art. Nucleic acid sequence identity can be assessed by the algorithm of BLAST version 2.1 advanced search. BLAST is a series of programs that are available online at see world wide web at ncbi.nlm.nih.gov/BLAST. The advanced blast search (see world wide web at ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S.F., Gish, W., Miller, W., Myers, E. W. & Lipman, D. J. (1990) "Basic, local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth, Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "analog" means an amino acid or nucleic acid sequence which has been modified as compared to the angiopoietin-1 sequences wherein the modification does not alter the utility of the sequence (e.g. as a Tie2 binding and/or activating agent) as described herein. The modified sequence or analog may have improved properties over the angiopoietin-1 sequences. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen et al. Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The disclosure also includes sequences that hybridize to the angiopoietin-1 sequences or a fragment thereof and maintain the property of binding and activating Tie2 when presented as a multimeric form. The term "sequence that hybridizes" means a nucleic acid sequence that can hybridize to a sequence under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.-16.6 (Log 10 [Na+])+0.41(%(G+C) −600/l). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5×sodium chloride/sodium citrate (SSC)/5×Denhardt's solution/1.0% SDS at Tm (based on the above equation)−5° C., followed by a wash of 0.2×SSC/0.1% SDS at 60° C.

Angiopoietin-1 may be modified to contain amino acid substitutions, insertions and/or deletions that do not alter the binding and/or activating properties of the protein. Conserved amino acid substitutions involve replacing one or more amino acids of the protein with amino acids of similar charge, size, and/or hydrophobicity characteristics. When only conserved substitutions are made the resulting analog should be functionally equivalent to angiopoietin-1. Non-conserved substitutions involve replacing one or more amino acids of the conjugate protein with one or more amino acids which possess dissimilar charge, size, and/or hydrophobicity characteristics.

Administration or use of a nucleic acid encoding Angiopoietin-1 or variant thereof includes administration or use of a vector containing the nucleic acid molecule and the necessary regulatory sequences for the transcription and translation of the inserted sequence.

Suitable regulatory sequences may be derived from a variety of sources, including bacterial, fungal, viral, mammalian, or insect genes (for example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by angiopoietin-1 sequences and/or its flanking regions.

The recombinant expression vectors used in the methods and uses described herein may also contain a selectable marker gene which facilitates the selection of host cells transformed or transfected with a recombinant molecule described herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance, transformant cells can be selected with G418. Cells that have incorporated the selectable marker gene will survive while the other cells die. This makes it possible to visualize and assay for expression of recombinant expression vectors and in particular to determine the effect of a mutation on expression and phenotype. It will be appreciated that selectable markers can be introduced on a separate vector from the nucleic acid of interest.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium chloride-mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303(5656): 371-3 (2004)).

Suitable mammalian cells include, among others: 293T cells, COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.).

Angiopoietin-2 Inhibitors

In another embodiment, the Tie2 activating agent, i.e. Tie2 agonist, comprises an inhibitor of angiopoietin-2.

An "angiopoietin-2 inhibitor" as used herein includes any substance that is capable of inhibiting the expression or activity of angiopoietin-2 and thus, includes substances that inhibit angiopoietin-2 or the interaction of angiopoietin-2 with the Tie2 receptor. Such inhibitors optionally include antisense nucleic acid molecules, siRNAs, proteins, antibodies (and fragments thereof), aptamers, peptibodies, small molecule inhibitors and other substances. In an embodiment, the inhibitor is a blocking antibody or fragment thereof against angiopoietin-2. In another embodiment, the inhibitor is a peptibody against angiopoietin-2. In one embodiment, the angiopoietin-2 has the amino acid sequence as shown in NP_001138. In another embodiment, the inhibitor is an antisense nucleic acid or an siRNA against an angiopoietin-2 nucleic acid molecule. In one embodiment, the angiopoietin-2 nucleic acid molecule has the nucleic acid sequence as shown in NM_001147.

The term "antisense nucleic acid" as used herein means a nucleic acid that is produced from a sequence that is inverted relative to its normal presentation for transcription. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine-substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "aptamer" as used herein refers to short strands of nucleic acids that can adopt highly specific 3-dimensional conformations. Aptamers can exhibit high binding affinity and specificity to a target molecule. These properties allow such molecules to specifically inhibit the functional activity of proteins. Thus, in another embodiment, the Ang2 inhibitor is an aptamer that binds and inhibits Ang2 activity.

The term "peptibody" as used herein refers to a recombinant protein that fuses a peptide region with the Fc region of IgG. Thus, in another embodiment, the Ang2 inhibitor is an Ang2 peptide inhibitor fused with the Fc region of IgG.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and domain antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Conventional methods can be used to prepare antibodies. For example, by using a peptide from angiopoietin or Tie2, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody-producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256:495-497, 1975) as well as other techniques such as the human B-cell hybridoma technique (Kozbor and Roder, Immunology Today 4:3, 72-79, 1983), the EBV-hybridoma technique to produce human monoclonal antibodies (Cole et al., "The EBV-Hybridoma Technique and its Application to Human Lung Cancer" in "Monoclonal Antibodies in Cancer Therapy", Allen R. Bliss, Inc. (1985), pages 77-96) and screening of combinatorial antibody libraries (Huse et al. Science 246:4935, 1275-1282, 1989). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for angiopoietin-2 or Tie2.

Chimeric antibody derivatives, i.e., antibody molecules that combine a non-human animal variable region and a human constant region are also contemplated. Chimeric antibody molecules can include, for example, the antigen binding domain from an antibody of a mouse, rat, or other species, with human constant regions. Conventional methods may be used to make chimeric antibodies containing the immunoglobulin variable region which recognizes angiopoietin-2 or Tie2 protein (See, for example, Morrison et al. (PNAS 81:21, 6851-6855, 1984), and Takeda et al. (Nature 314:452-454), and the patents of Cabilly et al., U.S. Pat. No. 4,816,567; Boss et al., U.S. Pat. No. 4,816,397; Tanaguchi et al., European Patent Publication No. EP171496; European Patent Publication No. 0173494, United Kingdom patent GB 2177096B).

Monoclonal or chimeric antibodies specifically reactive with angiopoietin-2 or Tie2 as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al. (1983) Proc. Natl. Acad. Sci. 80:12, 7308-7312), Kozbor and Roder (1983) Immunology Today 4:3, 72-79; Olsson et al. (1982) Methods in Enzymol. 92, 3-16, PCT Patent Application Publication No. WO92/06193 and EP Patent Application Publication No. 0 239 400). Humanized antibodies can also be commercially produced (Scotgen Limited, 2 Holly Road, Twickenham, Middlesex, Great Britain.)

Specific antibodies, or antibody fragments, reactive against angiopoietin-2 or Tie2 may also be generated by screening expression libraries encoding immunoglobulin genes, or portions thereof, expressed in bacteria with peptides produced from the nucleic acid molecules encoding a angiopoietin-2 or Tie2. For example, complete Fab fragments, VH regions and FV regions can be expressed in bacteria using phage expression libraries (See for example Ward et al. (1989) Nature 348:544-546, Huse et al. (1989) Science 246:4935, 1275-1282, and McCafferty et al. (1989) Nature 348, 552-555).

Antibodies may also be prepared using DNA immunization. For example, an expression vector containing a nucleic acid encoding angiopoietin-2 may be injected into a suitable animal such as mouse. The protein will therefore be expressed in vivo and antibodies will be induced. The antibodies can be isolated and prepared as described above for protein immunization.

The angiopoietin-2 inhibitors, the angiopoietin-1 peptides or the Tie2 binding peptides described herein may also contain or be used to obtain or design "peptide mimetics". For example, a peptide mimetic may be made to mimic the function of an angiopoietin-2 inhibitor. "Peptide mimetics" are structures which serve as substitutes for peptides in interactions between molecules (See Morgan et al. (1989), *Ann. Reports Med. Chem.* 24, 243-252 for a review). Peptide mimetics include synthetic structures which may or may not contain amino acids and/or peptide bonds but retain the structural and functional features of the protein, including binding to and/or activating Tie2. Peptide mimetics also include peptoids, oligopeptoids (Simon et al. (1992) Proc. Natl. Acad. Sci. 89, 9367-9371).

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins described herein. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Tie2 Binding Peptides Monomers and Multimeric Forms

In another embodiment, the Tie2 agonist is a binding and/or activating agent for use in the methods and uses described herein and comprises a multimeric form of a Tie2 binding peptide monomer thereof.

In one embodiment, the multimeric form comprises an even number of units of the monomer. In another embodiment, the multimeric form is a tetramer. In yet another embodiment, the multimeric form is a dimer. In yet other embodiments, the multimeric form comprises six, eight, ten or twelve units of the Tie2 binding peptide monomer. Higher order multimers can for example be multiple copies of a lower order multimer joined together. For example, an octamer could be two tetramers joined together. In another embodiment, the multimeric form comprises an odd number of units of the monomer. For example, the multimeric form can be a trimer or the multimeric form can comprise five, seven, nine or eleven units of the Tie2 binding peptide monomer. In a particular embodiment, the multimeric form is a tetramer.

The Tie2 binding peptide contained within the monomer is at least two amino acids in length, is at least five amino acids in length or is at least seven amino acids in length. An optional size range for the peptide is 7-25 amino acids in length, or 7-15 amino acids in length. Other size ranges include 5-30 amino acids in length, 5-40 amino acids in length, 5-50 amino acids in length, 5-60 amino acids in length, 5-70 amino acids in length, 5-80 amino acids in length, 5-90 amino acids in length or 5-100 amino acids in length. Optionally, the peptide is no more than 100 amino acids in length.

In one embodiment, the Tie2 binding peptide within the monomer comprises an amino acid sequence that is present in a native Tie2 ligand (e.g., an angiopoietin, such as Ang 1 or Ang 2). For example, a fragment of an angiopoietin that retains the ability to bind to Tie2 can be used as the Tie2 binding peptide, such as the fibrinogen-like domain (FLD), also called the receptor binding domain. Alternatively, in another embodiment, the Tie2 binding peptide within the monomer comprises an amino acid sequence that is not present in a native Tie2 ligand. It has been shown that peptides having amino acid sequences that differ from the primary sequence of angiopoietins can be selected that have affinity for Tie2 (see e.g., Tournaire, R. et al. (2004) *EMBO Reports* 5, 262-267). Such peptides can be identified, for example, by screening of a phage displayed peptide library (e.g., a random 7-mer library) for peptides that bind to Tie2 (e.g., a Tie2-Fc fusion protein), with confirmation of peptide binding to Tie2 by screening of the selected peptide for binding to Tie2 using an ELISA assay (e.g., as described in Tournaire, R. et al. (2004) supra).

In an embodiment, the Tie2 binding peptide used in the monomer binds to Tie2 with high affinity but does not substantially inhibit binding of an angiopoietin to Tie2. In such an embodiment, the multimeric form does not compete with native angiopoietins for binding to Tie2. For example, the Tie2 binding peptide binds to Tie2 with high affinity but does not substantially inhibit the binding of Ang 1 to Tie2. Additionally or alternatively, the Tie2 binding peptide binds to Tie2 with high affinity but does not substantially inhibit the binding of, for example, Ang 2 or Ang 4, to Tie2.

In an embodiment, the Tie2 binding peptide monomer comprises a T7 peptide. In one embodiment, the T7 peptide comprises an amino acid sequence: His-His-His-Arg-His-Ser-Phe (SEQ ID NO: 1). In another embodiment, the T7 peptide is modified to have an amino terminal cysteine residue added to it and, thus, in this embodiment, the T7 peptide comprises an amino acid sequence: Cys-His-His-His-Arg-His-Ser-Phe (SEQ ID NO: 2).

In another embodiment, the Tie2 binding peptide monomer comprises a GA3 peptide. In one embodiment, the GA3 peptide comprises an amino acid sequence: Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 3). In another embodiment, the GA3 peptide is modified to have an amino terminal cysteine residue added to it and, thus, in this embodiment, the GA3 peptide comprises an amino acid sequence: Cys-Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 4).

In yet another embodiment, the Tie2 binding peptide monomer comprises a T8 peptide. In one embodiment, the T8 peptide comprises an amino acid sequence: His-Pro-Trp-Leu-Thr-Arg-His (SEQ ID NO: 5). In another embodiment, the T8 peptide is modified to have an amino terminal cysteine residue added to it and, thus, in this embodiment, the T8 peptide comprises an amino acid sequence: Cys-His-Pro-Trp-Leu-Thr-Arg-His (SEQ ID NO: 6).

In yet another embodiment, the Tie2 binding peptide monomer comprises a T6 peptide. In one embodiment the T6 peptide comprises an amino acid sequence: Lys-Leu-Trp-Val-Ile-Pro-Lys (SEQ ID NO: 7). In another embodiment, the T6 peptide is modified to have an amino terminal cysteine residue added to it and, thus, in this embodiment, the T6 peptide comprises an amino acid sequence: Cys-Lys-Leu-Trp-Val-Ile-Pro-Lys (SEQ ID NO: 8).

In another embodiment, the Tie2 peptide binding monomer comprises a T4 peptide. In one embodiment, the T4 peptide comprises an amino acid sequence: Asn-Leu-Leu-Met-Ala-Ala-Ser (SEQ ID NO: 9). In another embodiment, the T4 peptide has an amino terminal cysteine residue added to it and, thus, in this embodiment, the T4 peptide comprises an amino acid sequence: Cys-Asn-Leu-Leu-Met-Ala-Ala-Ser (SEQ ID NO: 10).

The Tie2 binding peptides T4, T6, T7 and T8 also are described in Tournaire, R. et al. (2004) *EMBO Reports* 5, 262-267. The Tie2 binding peptide GA3 also is described in Wu, X. et al. (2004) *Biochem. Biophys. Res. Commun.* 315, 1004-1010.

The Tie2 binding peptides described herein may be modified to contain amino acid substitutions, insertions and/or deletions that do not alter the peptides ability to bind and/or activate Tie2. Conserved amino acid substitutions involve replacing one or more amino acids of the peptide with amino acids of similar charge, size, and/or hydrophobicity characteristics. When only conserved substitutions are made the resulting analog should be functionally equivalent to the peptide. Non-conserved substitutions involve replacing one or more amino acids of the peptide with one or more amino acids which possess dissimilar charge, size, and/or hydrophobicity characteristics.

The Tie2 binding peptides described herein may be modified to make them more therapeutically effective or suitable. For example, the peptides may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

In addition to the Tie2 binding peptide, the Tie2 binding peptide monomer can comprise other chemical moieties or groups, such as spacers and/or multimerizing groups. For example, the Tie2 binding peptide can be linked to a spacer, which may serve one or more functionalities. The spacer can, for example, function to increase the distance between the monomers when they are multimerized to facilitate interaction of the multimeric form with the Tie2 receptor (e.g., reduce steric hindrance). Additionally or alternatively, the spacer can, for example, serve as a chemical group by which the monomers can be multimerized and/or can contribute to the pharmacodynamics/pharmacokinetics of the compound. Moreover, the Tie2 binding peptide monomer can comprise one or more multimerizing groups, chemical moieties that function to facilitate multimerization of the monomers. A particular multimerizing group is a biotin group, which has affinity for avidin, streptavidin and neutravidin such that any of the three latter compounds can be used for multimerization of monomers comprising a biotin group. Another example of a multimerizing group is a coiled-coil domain, which can be linked to the amino terminus of the peptide through standard recombinant DNA engineering techniques and which self-assembles into oligomeric structures (see e.g., U.S. Patent Application Publication Nos. 2003/0220476 and 2006/0074230 for further description of the use of coiled coil domains for multimerization). Non-limiting examples of coiled-coil domains suitable for use are the coiled coil domains from the yeast transcription factor GCN4, from cartilage matrix protein (CMP) or from cartilage oligomeric matrix protein (COMP). Additional multimerizing agents using fused Fc domains resulting in a tetrameric configuration are provided in Davis et al. (2003) incorporated herein by reference (see in particular FIG. 1 of Davis et al.).

In one embodiment, the spacer is a polyethylene glycol (PEG) spacer, which is a polymeric molecule that can contain different numbers of units, such as 2, 4, 6, 8, 10, 11 or 12 units. PEG polymers are also known in the art as polyethylene oxide (PEO) polymers and thus the terms PEG and PEO as used herein are intended to be equivalent. Numerous other suitable spacers (also known as linkers) are well known in the art, non-limiting examples of which include other polyalkylene glycols, polyesters and polyalkylene amines. Moreover, a wide variety of spacers linked on one end to a reactive moiety and on the other end to a biotin group are commercially available (EZ-Link Biotin reagents available from Pierce Chemical Co., Rockford, Ill., USA) and can be used in the preparation of the Tie2 binding peptide monomers used with the methods and uses described herein. Non-limiting examples of commercially available reagents of the structure: reactive moiety-spacer-biotin include:

Sulfhydryl Reactive Reagents:
EZ-Link Biotin-BMCC (1-Biotinamido-4-(4'-[maleimidoethyl-cyclohexane]-carboxamido)butane)
EZ-Link Biotin-HPDP (N-(6-(Biotinamido)hexyl)-3'-(2'-pyridyldithio)-propionamide
EZ-Link Iodoacetyl-LC-Biotin (N-iodoacetyl-N-biotinylhexylenediamine)

EZ-Link Iodoacetyl-PEO$_2$ Biotin ((+)-Biotinyl-iodoacet-amidyl-3,6-dioxaoctanediamine)
EZ-Link Maleimide PEO$_n$-Biotin (n=2 or 11)
Amine Reactive Reagents:
EZ-Link NHS-PEO$_n$-Biotin (n=4 or 12)
EZ-Link NHS-SS-Biotin (succinimidyl 2-(biotinamido)-ethyl-1,3'-dithiopropionate)
EZ-Link Sulfo-NHS-LC-Biotin (Sulfosuccinimidyl-6-(biotinamido)hexanoate)
EZ-Link TFP-PEO$_3$-Biotin (Tetrafluorophenyl Ester PEO$_3$-biotin)
Carboxyl Reactive Reagents:
EZ-Link 5-(Biotinamido)pentylamine
EZ-Link Amine-PEO$_2$-Biotin Labeling Reagent ((+)-Biotinyl-3,6-dioxaoctanediamine)
EZ-Link Amine-PEO$_3$-Biotin Labeling Reagent ((+)-Biotinyl-3,6,9-trioxaundecanediamine)
EZ-Link Biotin PEO-Amine ((+)-Biotinyl-3,6-dioxaoctanediamine)
EZ-Link Biotin-PEO-LC-Amine ((+)-Biotinyl-3,6,9-trioxaundecanediamine)

Furthermore, a branched arm spacer can be linked to multiple copies of the Tie2 binding peptide as a means to multimerize the peptide. Non-limiting examples include 2 and 4 armed activated branched PEG spacers, although spacers with more arms, such as 8 or 12 armed activated branched PEG spacers also can be used. Branched activated PEG spacers (e.g., activated with maleimide) are commercially available (e.g., NOF Corporation, Tokyo, Japan).

In an embodiment, the Tie2 binding peptide monomer comprises a structure: A-B-C, wherein A comprises a Tie2 binding peptide, B comprises a spacer and C comprises a multimerizing group, wherein C has affinity for D, a multimer agent comprising multiple binding sites for C. In one embodiment, the multimer agent D has four binding sites for the multimerizing group C such that a tetramer is formed when four Tie2 binding peptide monomers, A-B-C, interact with the multimer agent D. In an embodiment, the multimerizing group, C, for use in creating tetramers is a biotin group. Optional multimer agents, D, for use in creating tetramers are avidin, streptavidin and neutravidin. It is well known in the art that avidin, streptavidin and neutravidin have four binding sites for biotin and that biotin binds with high affinity to each of avidin, streptavidin and neutravidin. An optional spacer, B, for use in a monomer of the structure A-B-C is a polyethylene glycol (PEG) spacer.

In another embodiment, the Tie2 binding peptide monomer comprises a structure: A-B, wherein A comprises a Tie2 binding peptide and B comprises a spacer, wherein the multimeric form is created by covalent linkage of multiple Tie2 binding peptides via the common spacer B. An optional spacer, B, for use in a monomer of the structure A-B is a polyethylene glycol (PEG) spacer.

In yet another embodiment, the Tie2 binding peptide monomer comprises a structure: A-B-C, wherein:
A comprises a Tie2 binding peptide selected from a T7 peptide and a GA3 peptide;
B comprises a polyethylene glycol spacer; and
C comprises a biotin group,
wherein four copies of A-B-C are associated with a tetramer agent, D, to create the tetramer form, the tetramer agent, D, being selected from the group consisting of avidin, streptavidin and neutravidin. A specific example of this embodiment is a compound in which A comprises a T7 peptide, B comprises a polyethylene glycol spacer and C comprises a biotin group, and wherein the tetramer agent D comprises avidin.

In yet another embodiment, the Tie2 binding peptide monomer comprises a structure A-B-C, wherein:
A comprises a Tie2 binding peptide;
B comprises a spacer; and
C comprises a multimerizing group.

Optionally, the Tie2 binding peptide, A, comprises a T7 peptide or a GA3 peptide. Alternatively, the Tie2 binding peptide can comprise, for example, a T8 peptide, a T6 peptide or a T4 peptide. In an embodiment, the spacer, B, comprises a polyethylene glycol spacer. In another embodiment, the multimerizing group, C, comprises a biotin group.

In yet a further embodiment, the multimeric form for use in the methods and uses described herein comprises a peptide dimer, comprising: (a) a first peptide chain; (b) a second peptide chain; and (c) a linking moiety connecting said first and second peptide chains, wherein said peptide dimer binds to and activates the Tie2 receptor. Optionally, the first peptide chain is a T7 peptide and/or the second peptide chain is a T7 peptide. In an embodiment, both the first and second peptide chains are T7 peptides. Alternatively, the first and second peptide chains independently can be selected from the group consisting of a T7 peptide, a GA3 peptide, a T4 peptide, a T6 peptide and a T8 peptide. In an embodiment, the first and second peptide chains are both the same type of peptide chain. Additional Tie2 binding peptides that can be used are described in further detail above.

Optionally, the linking moiety comprises one or more water-soluble polymers covalently bound to the first peptide chain and the second peptide chain. In one embodiment, the one or more water-soluble polymers are linear polymers. Optionally, the water-soluble polymer is a polyethylene glycol (PEG) (e.g., a linear PEG molecule). The PEG can have a molecular weight of less than about 50,000 Daltons. In one embodiment, the linear PEG has a molecular weight in the range of about 3,000 Daltons to about 20,000 Daltons. In various embodiments, the linear PEG has a molecular weight of about 3,000 Daltons, about 3,400 Daltons, about 5,000 Daltons or about 10,000 Daltons. It is understood that in a given preparation of PEG, the molecular weights will typically vary among individual molecules. Some molecules will weigh more, and some less, than the stated molecular weight. Such variation is generally reflected by use of the word "about" to describe the molecular weights of the PEG molecules.

In another embodiment, the multimeric form comprises dimers utilizing a linear PEG linker having a molecular weight less than about 20,000 Da, or having a molecular weight in the range of about 3,000 Daltons to about 10,000 Da.

In another embodiment, the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie2 receptor. In one embodiment, the first, second, third and fourth peptide chains are T7 peptides. Alternatively, the first, second, third and fourth peptide chains independently can be selected from the group consisting of a T7 peptide, a GA3 peptide, a T4 peptide, a T6 peptide and a T8 peptide, and optionally the first, second, third and fourth peptide chains are all the same type of peptide chain. Additional Tie2 binding peptides that can be used are described in further detail above.

In such an embodiment, the linking moiety comprises one or more water-soluble polymers covalently bound to the first, second, third and fourth peptide chains. In one embodiment, the one or more water-soluble polymers are branched chain polymers, such as a polyethylene glycol (PEG) (e.g., a branched chain PEG molecule). Optionally, the branched PEG has a molecular weight in the range of about 3,000 Daltons to about 50,000 Daltons. In various embodiments, the branched PEG has a molecular weight of about 3,000 Daltons, about 3,400 Daltons, about 5,000 Daltons, about 10,000 Daltons, about 20,000 Daltons, about 25,000 Daltons, about 30,000 Daltons, or about 40,000 Daltons. It is understood that in a given preparation of PEG, the molecular weights will typically vary among individual molecules. Some molecules will weigh more, and some less, than the stated molecular weight. Such variation is generally reflected by use of the word "about" to describe the molecular weights of the PEG molecules. In the case of a 20 kDa PEG for a tetramer, the arm length would be 5 kDa.

In the PEG-containing dimers, a single, optionally linear, PEG moiety is simultaneously attached to the termini (e.g., the N-termini) of both peptide chains of the peptide dimer. In the PEG-containing tetramers, a single, branched chain PEG moiety is simultaneously attached to the termini of the four peptide chains of the peptide tetramer. To prepare the PEG-containing dimeric and tetrameric compounds described above, Tie2 binding peptides can be reacted with activated PEG linkers (e.g., PEG dimaleimide for preparation of dimers, PEG tetramaleimide for preparation of tetramer. Such activated PEG linkers (linear or branched chain) are commercially available (e.g., from NOF America Corporation).

In addition to the dimers and tetramers described above, other multimeric forms comprising two or more Tie2 binding peptides linked by a linking moiety can be used, such as those containing three, five, six, seven, eight, nine, ten, eleven or twelve Tie2 binding peptides covalently linked to a linking moiety, optionally a branched linking moiety, such as a branched chain PEG molecule. Such alternative multimeric forms can be prepared as described for the dimers and tetramers, using linker moieties having the appropriate number of reactive ends (e.g., six reactive ends for a multimer containing six peptide chains) and the appropriate ratio of peptide to linker (e.g., 6:1 for a multimer containing six peptide chains). In such cases, larger PEG molecules are used to maintain a similar arm length between monomers. For example, a multimer of 8 monomers made with a 40 kDa PEG molecule would have an arm length of 5 kDa.

Alternative water-soluble polymer linkers include, but are not limited to, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols. For peptide dimers, the polymer linker can have a molecular weight of less than 20,000 Da. In one embodiment, the molecular weight is about 10,000 Da. For peptide tetramers, the polymer linker has a molecular weight of about 20,000 Da.

Other types of linking moieties known in the art can be used to join the peptide chains in the multimers (e.g., two peptide chains in the dimer, four peptide chains in the tetramer). Non-limiting examples of additional suitable linker moieties that can be used to join multiple peptide chains to form multimers include those described in US Patent Application Publication Nos. 2007/0104704 and US Publication 2007/0027074, the entire contents of both of which are expressly incorporated herein by reference.

In another embodiment, the Tie2 agonist comprises an agent that activates Tie2 without binding to Tie2. The activation may be direct or indirect. For example, an inhibitor of a Tie2 inhibitor indirectly activates Tie2. Accordingly, an inhibitor of a Tie2 inhibitor is a Tie2 activating agent/agonist. One example of an inhibitor of a Tie2 inhibitor is AKB9778 from Aerpio. Another example of an inhibitor of a Tie2 inhibitor is an antibody that inhibits VE-PTP (the target of AKB9778).

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Materials and Methods
Preparation of Vasculotide

T7 peptides were reacted with a 10 kDa tetrameric polyethylene glycol-maleimide. Specifically, activated PEG and T7 peptide were added to a 50 mL round bottom flask protected from light and PBS (pH 6.5, 22 mL) was added for a final peptide concentration of 5 mg/mL. The reaction was stirred at room temperature, the pH verified using a pH meter and the progress of the reaction monitored by HPLC at various time intervals. The reaction mixture was then acidified to pH 3.5 after which the following steps were performed:

Step 1 FLASH LC:
Column: Reverse Phase C18, Fuji, 200 A, 40 g column 30 μm (custom packed)
Gradient Profile: 10-100% B in 63 mins
Eluents: Eluent A=0.1% TFA in water, Eluent B=0.1% TFA in 60% acetonitrile, 40% water
Detection: UV (λ-210 nm/254 nm)
Column temp: room temperature
Flow Rate: 40 mL/min Step 2 Preparative HPLC:
Column: Reverse Phase C18, Daiso Bio C18, 200 A, 10 μm 25 mm×250 mm (custom packed)
Gradient Profile: 50-100% B in 70 mins
Eluents: Eluent A=0.1% HFBA in 3% acetonitrile in water, Eluent B=0.1% HFBA in 60% acetonitrile, 40% water
Detection: UV (λ-210 nm)
Column temp: room temperature
Flow Rate: 30 mL/min Step 3 Preparative HPLC:
Column: Reverse Phase C18, Daiso Bio C18, 200 A, 10 μm 25 mm×250 mm (custom packed)
Gradient Profile: 45-100% B in 77 mins
Eluents: Eluent A=0.1% TFA in water, Eluent B=0.1% TFA in 60% acetonitrile, 40% water
Detection: UV (λ-210 nm)
Column temp: room temp
Flow Rate: 30 mL/min Final material for QC was lyophilized after step 3 into a tared vial to determine the amount of material. This resulted in a 4-arm 10 kDa PEG maleimide (H-Cys(succinimido-propionylaminoethyl)-His-His-His-Arg-His-Ser-Phe-OH)$_4$-PEG 10 kDa trifluoroacetate salt.

Cells and Influenza and *Staphylococcus aureus* Infection

Primary human lung microvascular endothelial cells (HMVECs) obtained from Lonza were cultured in EBM-2 media with the recommended supplements and used in passages 6-9. Primary C57Bl/6 mouse lung microvascular endothelial cells were obtained from Cell Biologics (Chicago, Ill.) and were cultured with Mouse Endothelial Cell Medium with the recommended supplements. Influenza A X31 (H3N2) was used since the H3N2 subtype is most commonly associated with complications and death (Thompson et al., 2003); a clinical isolate (H3N2) was also used to confirm key findings. The virus was added to cells in serum-free media. After one hour, 0.5% serum was added. All infections were for 24 hours unless otherwise indicated. *S. aureus* (ATCC 29213) was heat-killed by incubation at 56° C. for 2 hours and added to cells at a multiplicity of infection of 100.

Permeability Assay

HMVECs seeded on 0.4 µm-pore polyester transwells (Costar) coated with Attachment Factor (Invitrogen) were grown to confluency for 3-4 days. Baseline permeability to fluorescein-Na was then measured as previously described (Armstrong et al., 2012). As a complementary approach, the transendothelial electrical resistance (TEER) of endothelial monolayers was measured using the Endohm-12 (WPI, Florida). Cells were then treated with influenza at different multiplicities of infection (MOI; defined as the ratio of plaque forming units to endothelial cells) for 24 hours. Permeability to fluorescein-Na and/or the TEER were then measured and compared to (pre-infection) baseline. For priming experiments, Vasculotide (VT) 2 ng/mL was added at the same time as the bacteria.

Mouse Model of Severe Influenza

C57Bl/6 mice were inoculated intranasally with X31 influenza (64-128 HAU/mouse) and lung vascular leak was assessed 4 days after infection. In some experiments, VT 400 ng or vehicle control was injected intraperitoneally immediately after infection and daily after that. Amantadine was given by oral gavage three times a day (46 mg/kg/mouse). Vascular leak was assessed by measuring wet/dry ratio of lungs or by quantifying Evans blue dye leak; Evans blue (EB) dye binds tightly to albumin and is a reproducible and accurate means to assess vascular permeability (Patterson et al., 1992). Ten minutes prior to euthanasia, 100 µL of 1% EB was injected via tail vein. 200 µL of whole blood was collected for EB measurement. The thorax was opened and the mouse perfused with 10 mL PBS to flush the vasculature, after which the lungs were harvested. EB was extracted from tissue by incubation in formamide and absorbances at 620 (A620) and 740 (A740) nm were recorded. EB content was calculated by correcting A620 for heme and converted to µg EB by comparing to a standard curve.

Results:

Mouse Model of Primary Viral Pneumonia and Acute Lung Injury

Figure 2:
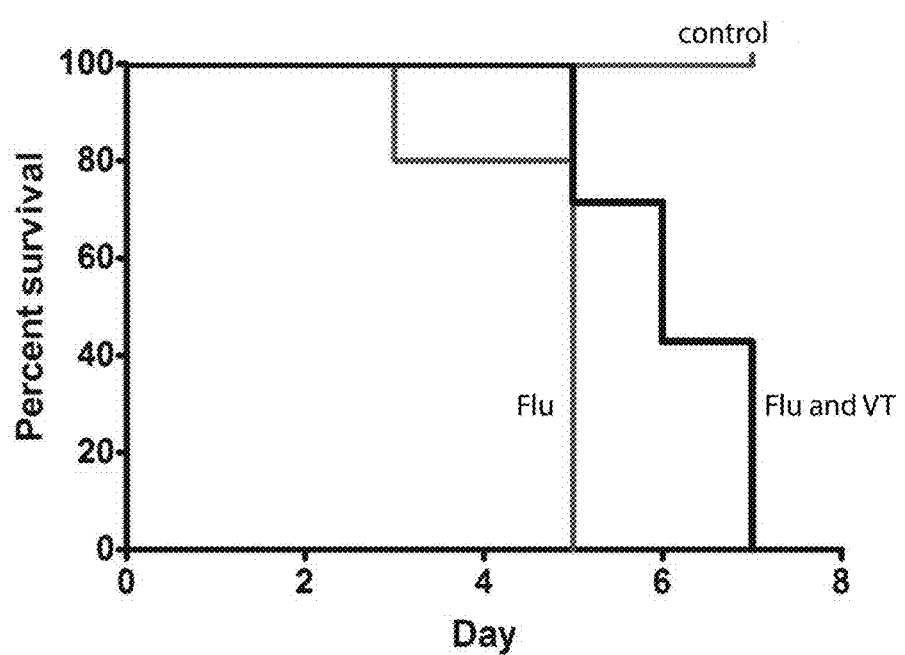
FIG. 2 shows that the Tie2-agonist peptide Vasculotide (VT) prolongs survival from severe influenza. C57Bl/6 mice were infected intranasally with 128 HAU influenza and received VT (400 ng) or vehicle intraperitoneally (IP) at the time of infection and daily. Data are from 2 experiments with 18 mice, *$p=0.0131$ by log-rank test.
Figure 3A:
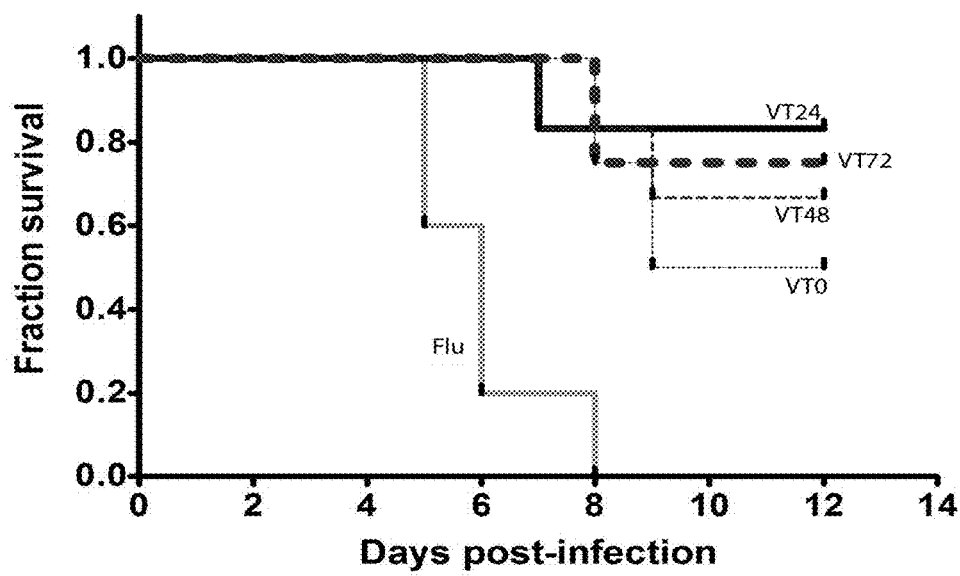
FIG. 3 shows that (A) the Tie2-agonist peptide Vasculotide (VT) increases survival from severe influenza even if administration is delayed, contrary to what would be expected from the literature where efficacy decreases if given in a delayed fashion. This has particular clinical relevance as the precise time of onset of infection (exposure to the virus) is often unknown. C57Bl/6 mice were infected intranasally with 64 HAU influenza (half of the dose used in FIG. 2) and received VT (400 ng) or vehicle intraperitoneally (IP) starting (VT0) at the time of infection or 24-72 hours later (VT24, VT48, VT72) and then daily. Numbers in brackets denote number of mice in each group. Data are from 2 experiments with 25 mice, *$p=0.0004$ by log-rank test for all curves; $p=0.0113$ for VT0 vs. flu alone; $p=0.0029$ for VT24 vs. flu alone; $p=0.0029$ for VT48 vs. flu alone; $p=0.0113$ for VT72 vs. flu alone; and (B) VT decreases influenza-induced hypothermia, even if given delayed. One-way ANOVA with Bonferroni post-test $p=0.0117$; $p<0.05$ for flu alone compared to VT0, VT24 and VT72.
Figure 3B:
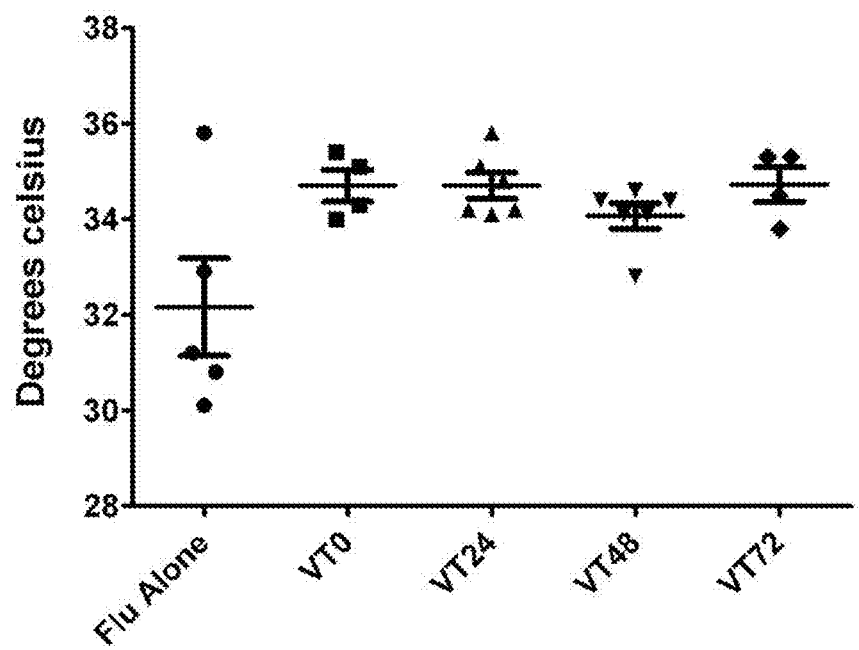
Figure 4:
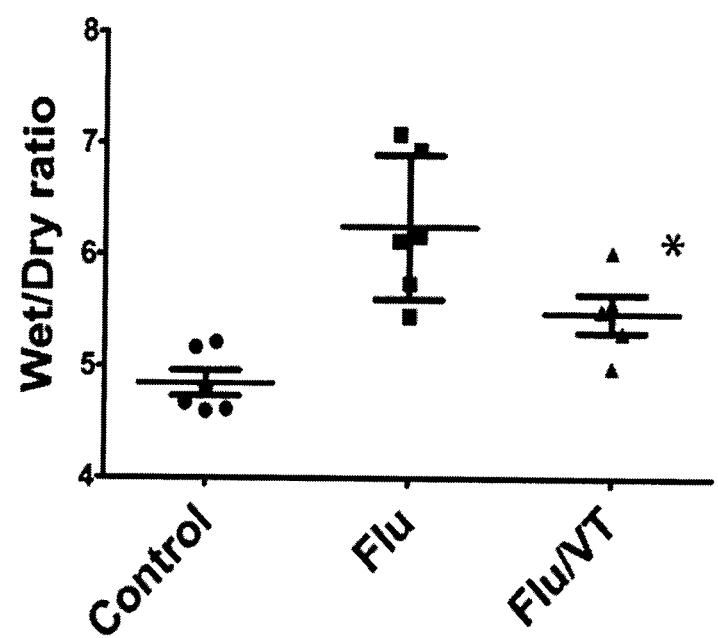
FIG. 4 shows the effect of Vasculotide on lung edema. Vasculotide (400 ng, IP daily) reduces lung microvascular leak as measured by wet/dry ratio on day 3 after infection, $p=0.0005$ by one-way ANOVA and $p<0.05$ for Flu vs. Flu/VT and Control vs. Flu by Bonferonni's Multiple Comparison Test. n=18 mice from 2 experiments.
Figure 5:
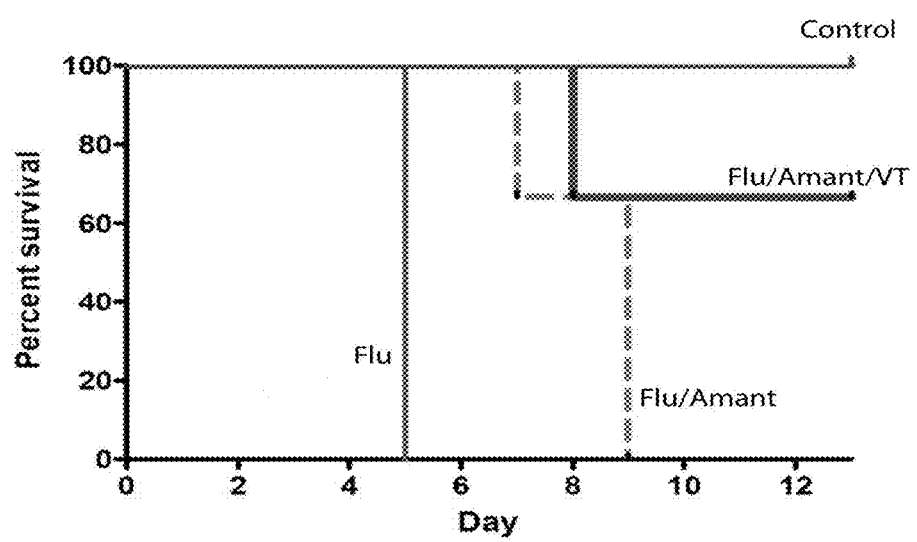
FIG. 5 shows that Vasculotide (400 ng IP, daily) increases mouse survival when administered simultaneously with the antiviral drug amantadine (Amant; 46 mg/kg/day in 3 divided doses). *$p=0.02$ by log-rank (Mantel-Cox) test, n=12 mice from 1 experiment. Mice were infected with 128 HAU influenza.
Figure 6A:
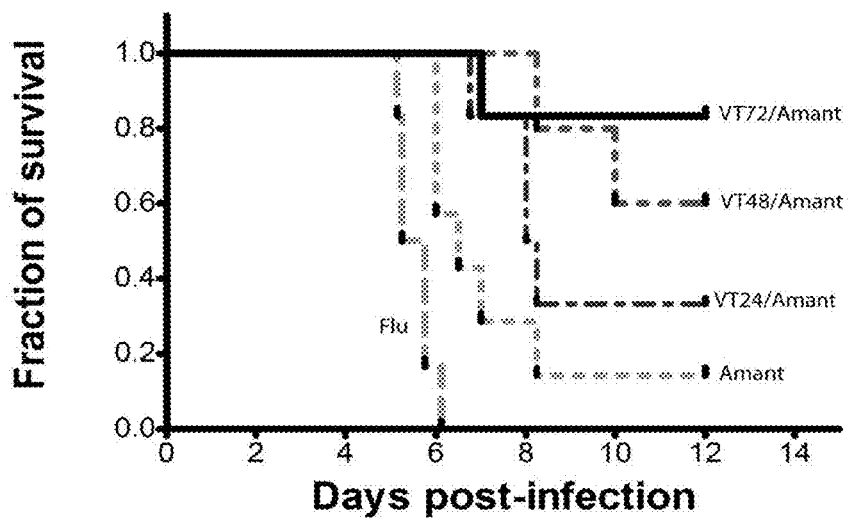
FIG. 6 shows that (A) Vasculotide (400 ng IP, daily) increases mouse survival when administered with the antiviral drug amantadine (Amant; 46 mg/kg/day in 3 divided doses) even if VT was administered 24-72 hours later (VT24, VT48, VT72; numbers in brackets denotes numbers of mice per group). *$p<0.0001$ by log-rank (Mantel-Cox) test, n=30 mice from 3 experiments. $P=0.03$ for Amant vs VT48/Amant, $p=0.01$ for Amant vs. VT72/Amant; These data (and those in FIG. 5) demonstrate that VT does not diminish the efficacy of antiviral drugs and that VT could therefore be safely given in concert with antiviral drugs. Mice were infected with 64 HAU of influenza, half the dose used in FIG. 5. (B) (baseline) and (C) (day 4) show that VT significantly improves oxygenation even if given 24-72 hours after infection; $p<0.0001$ by one-way ANOVA with Bonferroni's multiple comparison test. $P<0.05$ for Amant vs VT24/Amant; $p<0.05$ for Amant vs VT48/Amant, $p<0.05$ for Amant vs VT72/Amant. (D) VT tends to prevent flu-induced hypothermia; $p=0.06$ by one-way ANOVA with Tukey's test. (E) VT decreases flu-induced weight loss, even if given 48 hours after infection; $p=0.0158$ by one-way ANOVA; $p<0.05$ for VT48/Amant vs. Amant alone.
Figure 6B:
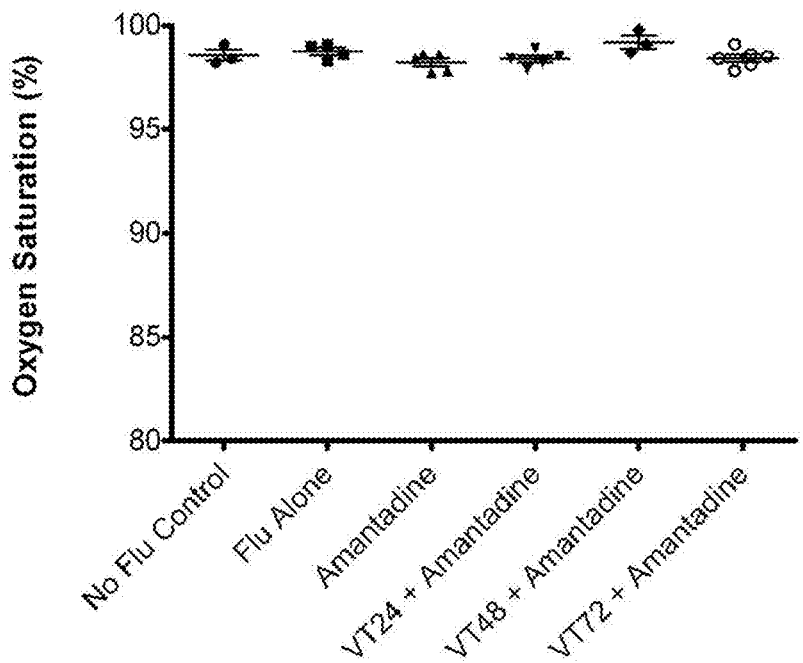
Figure 6C:
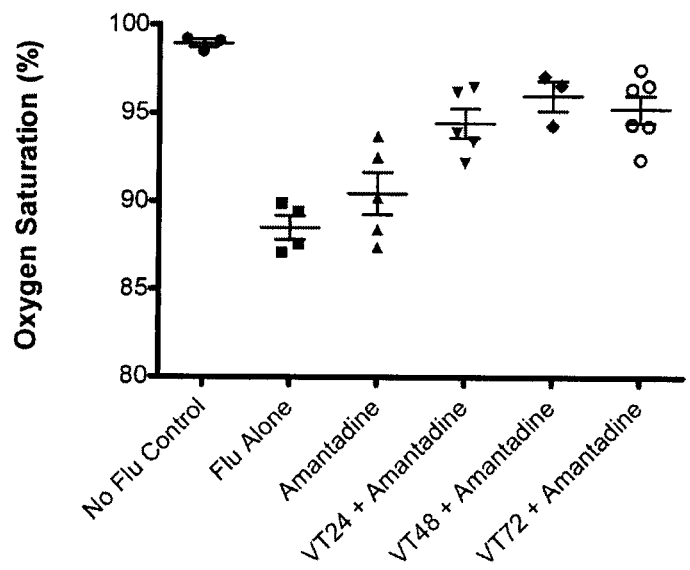
Figure 6D:
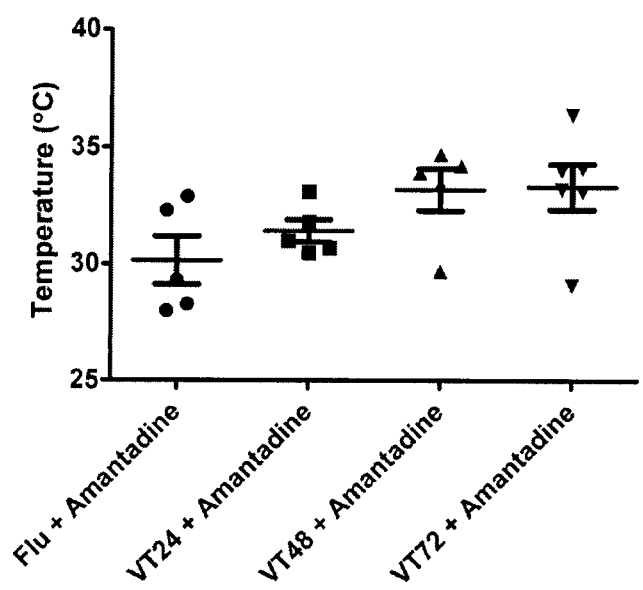
Figure 6E:
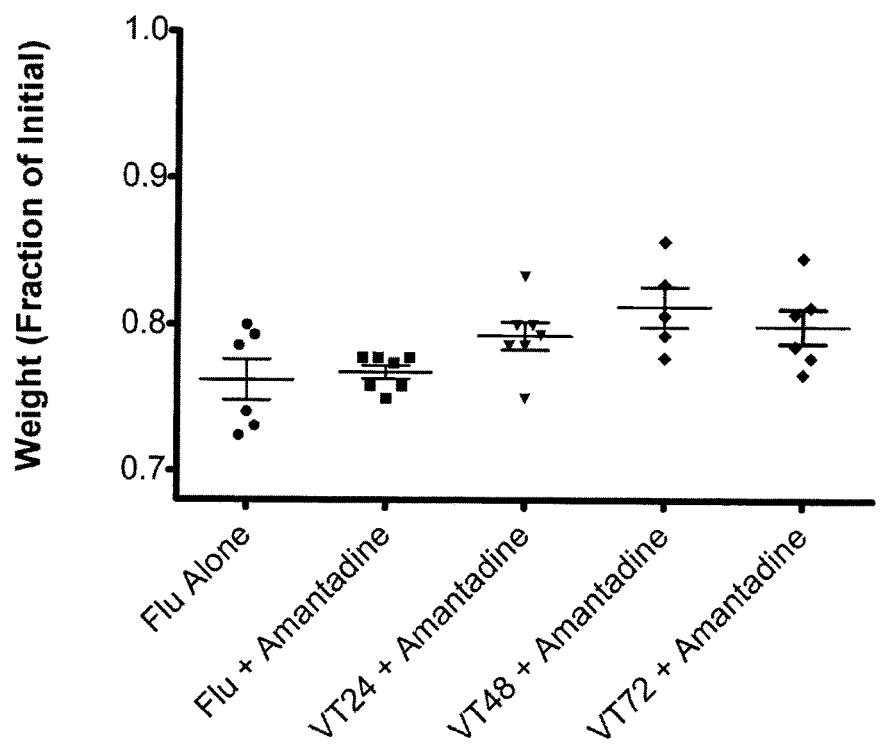
Figure 7:
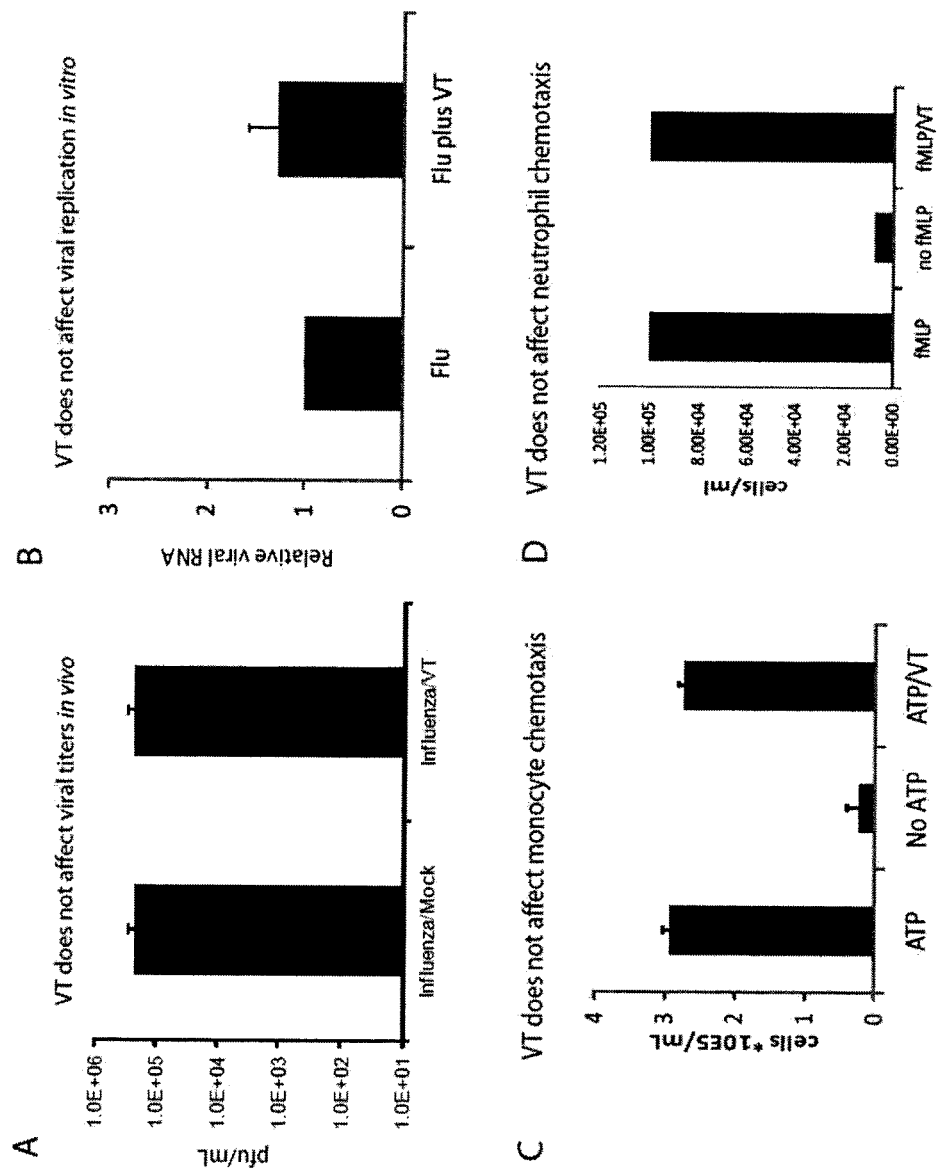
FIG. 7 shows that Vasculotide's beneficial effects are mediated by action on the endothelium and are not due to impaired viral replication. (A) Viral plaque forming units were measured 4 days after infection from mouse lung homogenates (n=3 per group) and corrected for lung weight; mice received 400 ng of Vasculotide (or vehicle) IP daily. (B) Influenza was added to primary human lung microvascular endothelium for 1 hour, then cells were rinsed to remove uninternalized virus. Vasculotide (2 ng/mL) was then added. Viral replication was quantified by qPCR for influenza A M1 protein after 24 hours using 18S RNA as a reference. Results are mean and SD from 3 experiments. (C) The benefit of Vasculotide is not due to impaired leukocyte chemotaxis. Human (THP-1) monocytes were incubated with 2 ng/mL VT or vehicle, then were allowed to migrate across a transwell in response to ATP (10 uM). The number of migrated cells was counted. Similar results were obtained with mouse J774 monocytes. (D) Vasculotide also has no effect on neutrophil chemotaxis. The same experiment was performed as in FIG. 5C, but using human neutrophils exposed to 10 nM formyl-Methionyl-Leucyl-Phenylalanine peptide (fMLP).

C57Bl/6 mice infected with influenza (H3N2, 128 HAU/mouse) develop weight loss (FIG. 1D) and marked lung edema (FIG. 1A-C, E), dying approximately 5 days after infection. Administration of VT (400 ng, intraperitoneally daily, at the time of infection, significantly prolonged survival of infected mice (p<0.001) (FIG. 2). In a less severe model of influenza in which mice are given 64 HAU of influenza, infected mice die between 5 and 8 days after infection. Administration of VT (400 ng, intraperitoneally daily) even when given in a delayed fashion (FIG. 3A), significantly increased survival. In addition, VT decreased influenza-induced hypothermia (FIG. 3B) and reduced lung edema significantly (FIG. 4). When co-administered with the antiviral drug Amantadine, VT significantly increased survival of flu-infected mice compared to controls using both the higher (FIG. 5) and lower dose (FIG. 6A) of influenza. The benefit of VT was observed even if given as long as 72 hours after the infection (FIG. 6A). VT significantly improved arterial oxygen levels in infected mice (FIG. 6B-C), decreased influenza-induced hypothermia (FIG. 6D) and attenuated influenza-induced weight loss (FIG. 6E). Remarkably, VT itself has no intrinsic antiviral activity and no effect on leukocyte chemotaxis (FIG. 7). Without being bound by theory, it is believed that the mechanism of benefit is by action of VT on the endothelium. Another possible explanation is that VT acts on non-endothelial cell types that express Tie2, such as Tie2-expressing leukocyte populations.

In Vitro and In Vivo Model of Sequential Infection with Influenza Followed by *S. aureus*

Figure 8:
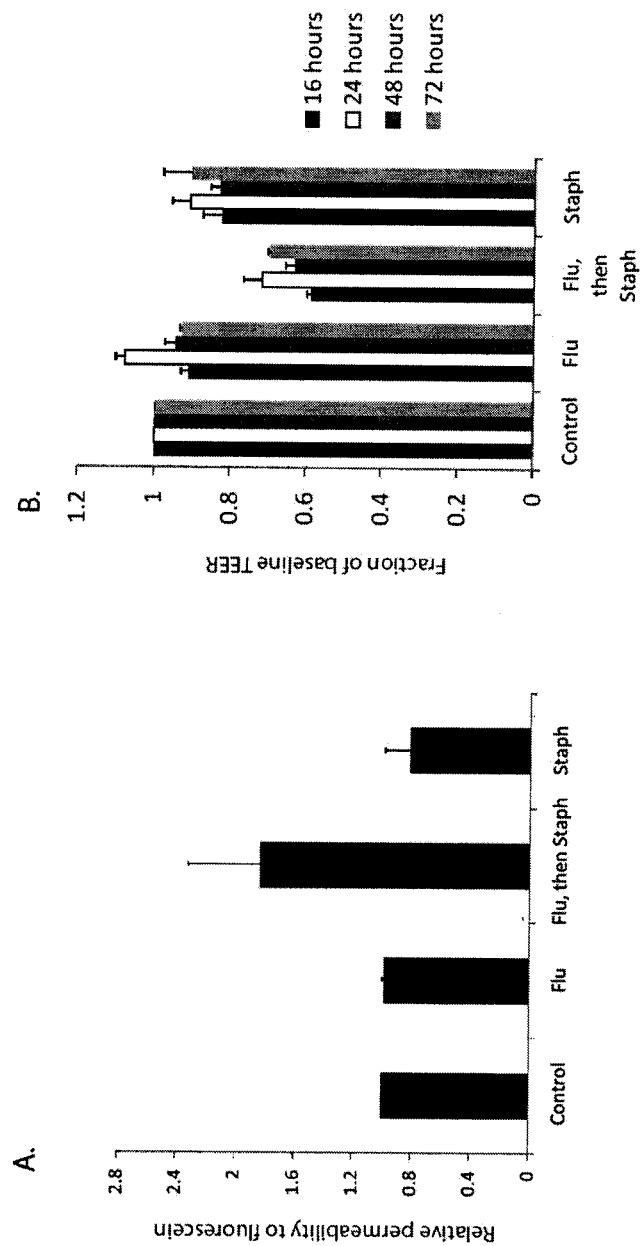
FIG. 8 shows that prior infection with influenza leads to synergistic endothelial permeability upon exposure to S. aureus that is independent of endothelial polarity. (A) Human lung microvascular endothelium seeded on transwells was infected with influenza at a multiplicity of infection (MOI) of 0.1. 16 hours later, heat-killed S. aureus was added ($10^7$ cfu/mL) for 24 hours and the permeability to fluorescein-Na (1 ug/mL) was measured. (B) The effect of increasing the time interval between flu and S. aureus: S. aureus was added 16-72 hours after influenza and the transendothelial electrical resistance (TEER) was measured 24 hours later. At each time point, the sequential infection by influenza and S. aureus induced a marked loss of barrier integrity that is greater than the sum due to either infection alone. Data are mean and SD from 3 independent experiments. (C) Cells treated as in (B) but cells were infected with influenza, MOI 1.0, 24 hours. Increased leak after S. aureus still occurs. (D) Priming still occurs after basolateral infection of the endothelium. Cells were treated as in (C), but cells were infected with influenza at the basal membrane for 24 hours. (E) Priming is order-specific: heat-killed S. aureus was added first to the endothelium for 24 hours, followed by influenza (MOI 0.1) for 24 hours. Infection with bacteria first followed by the virus does not induce greater leak. (F) Influenza does not increase attachment/internalization of S. aureus. Lung endothelium was infected with influenza (MOI 1) for 24 hours, then $10^7$ cfu/mL S. aureus were added. After 40 minutes, cells were rinsed 3 times to remove unbound or non-internalized bacteria. Cells were then lysed and adherent and internalized bacteria were plated.
Figure 8:
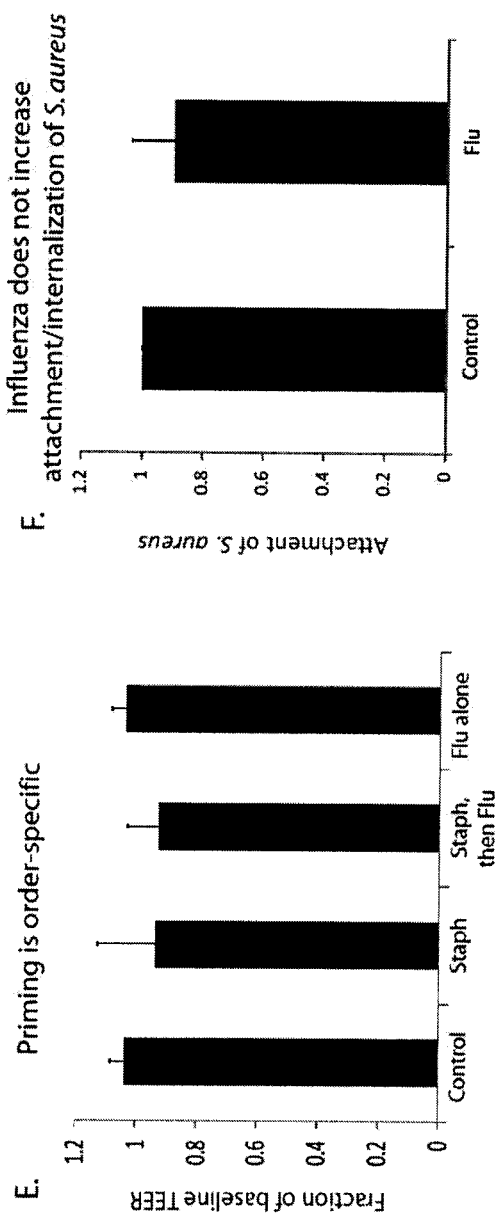
Figure 9A:
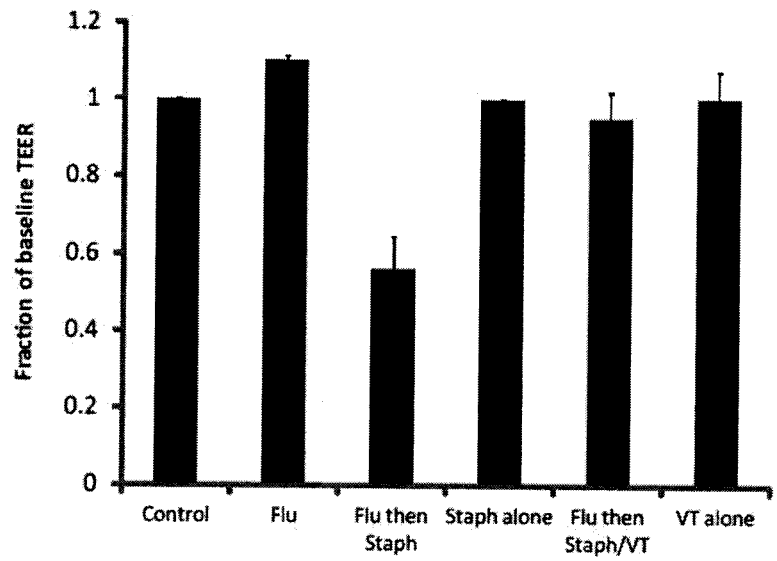
FIG. 9 shows (A) that Vasculotide prevents priming-induced endothelial permeability in vitro. Human lung endothelium infected with flu (MOI 0.1) for 24 hours followed by S. aureus with or without 2 ng/mL Vasculotide. The transendothelial electrical resistance (TEER) was measured 24 hours later and compared to baseline. (B) Vasculotide prevents priming-induced vascular leak in vivo. Lung edema (lung wet/dry ratio) after infection of C57/BL6 mice with influenza (32HAU) followed 3 days later by tail-vein injection of heat-killed S. aureus (staph). 12 hours later, mice were euthanized and lung edema was measured. In one group of mice, VT (400 ng) was given 4 hours prior to S. aureus. N=11 from one experiment; p<0.05 for flu/staph versus flu alone and for flu/staph/VT versus flu/staph. (C) Vasculotide attenuates cleavage of caspase-3 caused by sequential infection. Western blots for cleaved caspase-3 in cells infected with flu (MOI 0.1) for 24 hours followed by S. aureus with or without 2 ng/mL Vasculotide are shown. Beta-actin was the loading control.
Figure 9B:
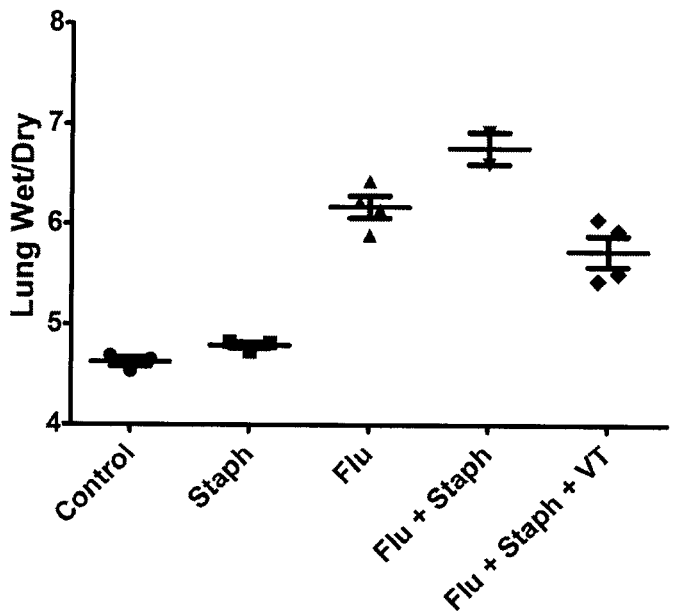
Figure 9C:
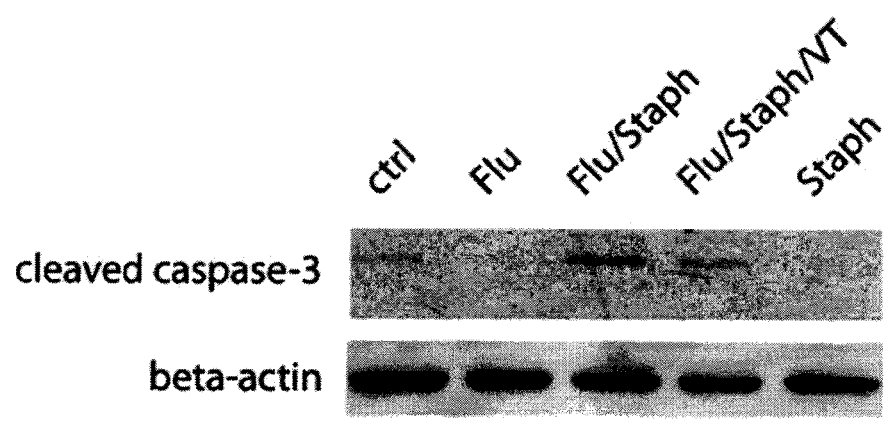

The data indicate that prior infection with influenza (MOI 0.1-1.0), even days earlier, leads to a marked increase in lung endothelial permeability upon exposure to *S. aureus* (FIG. 8A-C). The leak after sequential infection is greater than either infection alone (i.e. it is synergistic) and is independent of endothelial polarity (FIG. 8D); it is also order-specific, since adding *S. aureus* before influenza does not have the same effect (FIG. 8E). In addition, leak is not due to enhanced adhesion of the bacteria to the endothelium (FIG. 8F). Importantly, VT was able to almost completely prevent priming-induced leak despite having no effect on viral replication (FIG. 9A). The beneficial effect of VT was also seen in vivo (FIG. 9B). Leak appears to occur due to apoptosis, since sequential infection induces lung endothelial apoptosis, an effect that is attenuated by VT (FIG. 9C).

Summary

Enhancing or agonizing Tie2 activity, demonstrated using Vasculotide, significantly increases survival in a mouse model of severe human influenza and increases survival when co-administered with an antiviral drug, even if administered in a delayed fashion. Traditional treatment for influenza using antiviral drugs is most effective if given at the time of infection, and becomes progressively less effective over time. Since patients cannot be certain of the exact time of infection, the persistent benefit of delayed administration of VT is of clinical relevance. In addition, low-dose exposure to flu primes the lung endothelium to become leaky upon subsequent exposure (even days later) to bacteria; this effect is blocked by Vasculotide.

Leakiness of the lung endothelium is an important determinant of mortality from severe human influenza, and administration of Vasculotide is a therapy for treating both primary viral pneumonia and for decreasing lung edema and mortality after a bacterial superinfection.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Table of Sequences

| SEQ ID NO | SEQUENCE | DESCRIPTION |
|---|---|---|
| 1 | His His His Arg His Ser Phe | Peptide; Artificial Sequence T7 |
| 2 | Cys His His His Arg His Ser Phe | Peptide; Artificial Sequence T7 |
| 3 | Trp Thr Ile Ile Gln Arg Arg Glu Asp Gly Ser Val Asp Phe Gln Arg Thr Trp Lys Glu Tyr Lys | Peptide; Artificial Sequence GA3 |
| 4 | Cys Trp Thr Ile Ile Gln Arg Arg Glu Asp Gly Ser Val Asp Phe Gln Arg Thr Trp Lys Glu Tyr Lys | Peptide; Artificial Sequence GA3 |
| 5 | His Pro Trp Leu Thr Arg His | Peptide; Artificial Sequence T8 |
| 6 | Cys His Pro Trp Leu Thr Arg His | Peptide; Artificial Sequence T8 |
| 7 | Lys Leu Trp Val Ile Pro Lys | Peptide; Artificial Sequence T6 |
| 8 | Cys Lys Leu Trp Val Ile Pro Lys | Peptide; Artificial Sequence T6 |
| 9 | Asn Leu Leu Met Ala Ala Ser | Peptide; Artificial Sequence T4 |
| 10 | Cys Asn Leu Leu Met Ala Ala Ser | Peptide; Artificial Sequence T4 |

REFERENCES

Anna Majury M. D., O.A.o.M.L. (2005). www.oaml.com/pps/Laboratory-Working-Group.pps. Feb. 17, 2012

Armstrong, S. M., Khajoee, V., Wang, C., Wang, T., Tigdi, J., Yin, J., Kuebler, W. M., Gillrie, M., Davis, S. P., Ho, M., et al. (2012). Co-regulation of transcellular and paracellular leak across microvascular endothelium by dynamin and rac. Am J Pathol 180, 1308-1323.

Cho, C. H., Kammerer, R. A., Lee, H. J., Yasunaga, K., Kim, K. T., Choi, H. H., Kim, W., Kim, S. H., Park, S. K., Lee, G. M. & Koh, G. Y. Designed angiopoietin-1 variant, COMP-Ang1, protects against radiation-induced endothelial cell apoptosis. Proc. Natl. Acad. Sci. U.S.A 101, 5553-5558 (2004a).

Cho, C. H., Kammerer, R. A., Lee, H. J., Steinmetz, M. O., Ryu, Y. S., Lee, S. H., Yasunaga, K., Kim, K. T., Kim, I., Choi, H. H., Kim, W., Kim, S. H., Park, S. K., Lee, G. M. & Koh, G. Y. COMP-Ang1: a designed angiopoietin-1 variant with nonleaky angiogenic activity. Proc. Natl. Acad. Sci. U.S.A 101, 5547-5552 (2004b).

David S., Ghosh C. C., Kumpers P., Shushakova N., Van Slyke P., Khankin E. V., Karumanchi S. A., Dumont D., and Parikh S. M. (2011). Effects of a synthetic PEG-ylated Tie-2 agonist peptide on endotoxemic lung injury and mortality. Am J Physiol Lung Cell Mol Physiol 300:L851-L862.

Davis S., Papadopoulos N., Aldrich T. H., Maisonpierre P. C., Huang T., Kovac L., Xu A., Leidich R., Radziejewska E., et al. (2003) Angiopoietins have distinct modular domains essential for receptor binding, dimerization and superclustering. Nat Struct Biol 10(1):38-44.

Dominguez-Cherit, G., Lapinsky, S. E., Macias, A. E., Pinto, R., Espinosa-Perez, L., de la Torre, A., Poblano-Morales, M., Baltazar-Torres, J. A., Bautista, E., Martinez, A., et al. (2009). Critically Ill patients with 2009 influenza A(H1N1) in Mexico. Jama 302, 1880-1887.

Falsey, A. R., and Walsh, E. E. (2006). Viral pneumonia in older adults. Clin Infect Dis 42, 518-524.

Iverson, A. R., Boyd, K. L., McAuley, J. L., Plano, L. R., Hart, M. E., and McCullers, J. A. (2011). Influenza Virus Primes Mice for Pneumonia From *Staphylococcus aureus*. J Infect Dis 203, 880-888.

Kuiken, T., and Taubenberger, J. K. (2008). Pathology of human influenza revisited. Vaccine 26 Suppl 4, D59-66.

Kumpers P., Gueler F., David S., Van Slyke P., Dumont D. J., Park J-K, Bockmeyer C. L., Parikh S. M., Pavenstadt H., Haller H. and Shushakova. (2011). The synthetic Tie2 agonists peptide Vasculotide protects against vascular leakage and reduces mortality in murine abdominal sepsis. Crit Care 15:R261

Kuster, S. P., Drews, S., Green, K., Blair, J., Davis, I., Downey, J., Fowler, R., Katz, K., Lapinsky, S., McRitchie, D., et al. (2010). Epidemiology of influenza-associated hospitalization in adults, Toronto, 2007/8. Eur J Clin Microbiol Infect Dis 29, 835-843.

Lee, W. L., and Slutsky, A. S. (2001). Ventilator-induced lung injury and recommendations for mechanical ventilation of patients with ARDS. Semin Respir Crit Care Med 22, 269-280.

Louria, D. B., Blumenfeld, H. L., Ellis, J. T., Kilbourne, E. D., and Rogers, D. E. (1959). Studies on influenza in the pandemic of 1957-1958. II. Pulmonary complications of influenza. J Clin Invest 38, 213-265.

Maines, T. R., Szretter, K. J., Perrone, L., Belser, J. A., Bright, R. A., Zeng, H., Tumpey, T. M., and Katz, J. M. (2008). Pathogenesis of emerging avian influenza viruses in mammals and the host innate immune response. Immunol Rev 225, 68-84.

McGeer, A., Green, K. A., Plevneshi, A., Shigayeva, A., Siddiqi, N., Raboud, J., and Low, D. E. (2007). Antiviral therapy and outcomes of influenza requiring hospitalization in Ontario, Canada. Clin Infect Dis 45, 1568-1575.

Mohan, S. S., Nair, V., and Cunha, B. A. (2005). Post-viral influenza *Streptococcus pneumoniae* pneumonia in an intravenous drug abuser. Heart Lung 34, 222-226.

Mura, M., Binnie, M., Han, B., Li, C., Andrade, C. F., Shiozaki, A., Zhang, Y., Ferrara, N., Hwang, D., Waddell, T. K., et al. (2010) Functions of type II pneumocyte-derived vascular endothelial growth factor in alveolar structure, acute inflammation, and vascular permeability. Am J Pathol 176, 1725-1734.

Oseasohn, R., Adelson, L., and Kaji, M. (1959). Clinico-pathologic study of thirty-three fatal cases of Asian influenza. N Engl J Med 260, 509-518.

Patterson, C. E., Rhoades, R. A., and Garcia, J. G. (1992). Evans blue dye as a marker of albumin clearance in cultured endothelial monolayer and isolated lung. J Appl Physiol 72, 865-873.

Peltola, V. T., and McCullers, J. A. (2004). Respiratory viruses predisposing to bacterial infections: role of neuraminidase. Pediatr Infect Dis J 23, S87-97.

Procopio, W. N., Pelavin, P. I., Lee, W. M. & Yeilding, N. M. Angiopoietin-1 and -2 coiled coil domains mediate distinct homo-oligomerization patterns, but fibrinogen-like domains mediate ligand activity. J. Biol. Chem. 274, 30196-30201 (1999).

Schanzer, D. L., Tam, T. W., Langley, J. M., and Winchester, B. T. (2007). Influenza-attributable deaths, Canada 1990-1999. Epidemiol Infect 135, 1109-1116.

Speshock, J. L., Doyon-Reale, N., Rabah, R., Neely, M. N., and Roberts, P. C. (2007). Filamentous influenza A virus infection predisposes mice to fatal septicemia following superinfection with *Streptococcus pneumoniae* serotype 3. Infect Immun 75, 3102-3111.

Teijaro, J. R., Walsh, K. B., Cahalan, S., Fremgen, D. M., Roberts, E., Scott, F., Martinborough, E., Peach, R., Oldstone, M. B., and Rosen, H. (2011). Endothelial cells are central orchestrators of cytokine amplification during influenza virus infection. Cell 146, 980-991.

Thompson, W. W., Shay, D. K., Weintraub, E., Brammer, L., Cox, N., Anderson, L. J., and Fukuda, K. (2003). Mortality associated with influenza and respiratory syncytial virus in the United States. Jama 289, 179-186.

Tsigkos, S., Koutsilieris, M. & Papapetropoulos, A. Angiopoietins in angiogenesis and beyond. Expert Opin. Investig. Drugs. 12, 933-941 (2003).

VanSlyke, P., Alami, J. M. D., Kuliszewski, M. A., Leong-Poi, H., Sefton, M. & Dumont, D. J. Acceleration of diabetic wound healing by an angiopoietin eptidemimetic. eptide mimetic. Tissue Eng Part A 15(6), 1269-1280 (2009).

Ward N. L. & Dumont, D. J. The angiopoietins and Tie2/Tek: adding to the complexity of cardiovascular development. Semin. Cell Dev. Biol. 13, 19-27(2002).

Ward, N. L., Van Slyke, P. & Dumont, D. J. Functional inhibition of secreted angiopoietin: a novel role for angiopoietin 1 in coronary vessel patterning. Biochem. Biophys. Res. Commun. 323, 937-946 (2004).

The invention claimed is:

1. A method of treating an animal infected with influenza or with a bacterial superinfection associated with influenza comprising administering a multimeric form of Tie2 binding peptide monomers to the animal in need thereof; wherein each peptide monomer comprises:
   (i) a T7 peptide (SEQ ID NO:1) or a T7 modified peptide (SEQ ID NO:2),
   (ii) a GA3 peptide (SEQ ID NO:3) or a GA3 modified peptide (SEQ ID NO:4),
   (iii) a T4 peptide (SEQ ID NO:9) or a T4 modified peptide (SEQ ID NO:10);
   (iv) a T6 peptide (SEQ ID NO:7) or a T8 modified peptide (SEQ ID NO:8); or
   (v) a T8 peptide (SEQ ID NO:5) or a T8 modified peptide (SEQ ID NO:6);
   wherein the Tie2 binding peptide monomers are multimerized via a linking moiety, spacer and/or multimerizing agent; and wherein the animal is human and the influenza is human influenza.

2. The method of claim 1, further comprising administering an antiviral agent concurrently or sequentially.

3. The method of claim 2, wherein the antiviral agent is amantadine, rimantadine, zanamivir, peramivir, viramidine, ribavirin or oseltamivir.

4. The method of claim 1, wherein the Tie2 binding peptide monomer comprises a T7 peptide as shown in the amino acid sequences of SEQ ID NOs: 1 or 2 or a GA3 peptide as shown in the amino acid sequences of SE Q ID NOs: 3 or 4.

5. The method of claim 1, wherein the Tie2 binding peptide monomer comprises a peptide selected from the group consisting of a T4 peptide, a T6 peptide and a T8 peptide as shown in the amino acid sequences of SEQ ID NOs: 5-10.

6. The method of claim 1, wherein the multimeric form is a dimer, comprising: (a) a first peptide chain; (b) a second peptide chain; and (c) a linking moiety connecting said first and second peptide chains.

7. The method of claim 6, wherein the first peptide chain is a T7 peptide (SEQ ID NOs: 1 or 2) and/or the second peptide chain is a T7 peptide (SEC) ID NOs: 1 or 2).

8. The method of claim 6, wherein the linking moiety comprises one or more polyethylene glycol polymers covalently bound to the first peptide chain and the second peptide chain.

9. The method of claim 1, wherein the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains.

10. The method of claim 9, wherein the first, second, third and fourth peptide chains are T7 peptides (SEQ ID NOs: 1 or 2).

11. The method of claim 9, wherein the linking moiety comprises one or more branched polyethylene glycol (PEG) polymers covalently bound to the first, second, third and fourth peptide chains, the PEG having a molecular weight in a range of about 3,000 Daltons to about 20,000 Daltons.

12. The method of claim 9, wherein the first, second, third and fourth peptide chains are T7 peptides (SEQ ID NOs: 1 or 2) and the linking moiety is PEG, the PEG having a molecular weight of about 10,000 Daltons.

13. The method sf claim 1, for treating a bacterial superinfection associated with human influenza.

14. The method of claim 1, wherein the multimeric form of Tie2 binding peptide monomers is administered to the human at least 24 hours post-infection.

15. The method of claim 1, wherein the multimeric form of Tie2 binding peptide monomers is administered to the human at least 48 hours post-infection.

16. The method of claim 1, wherein the multimeric form of Tie2 binding peptide monomers is administered to the human at least 72 hours post-infection.

17. A composition comprising (a) a multimeric form of Tie2 binding peptide monomers and (b) an antiviral agent; wherein each peptide monomer comprises:
   (i) a T7 peptide (SEQ ID NO:1) or a T7 modified peptide (SEQ ID NO: 2);
   (ii) a GA3 peptide (SEQ ID NO:3) or a GA3 modified peptide (SEQ ID NO:4);
   (iii) a T4 peptide (SEQ ID NO:9) or a T4 modified peptide (SEQ ID NO:10);
   (iv) a T6 peptide (SEQ ID NO:7) or a T6 modified peptide (SEQ ID NO:8); or
   (v) a T8 peptide (SEQ ID NO:5) or a T8 modified peptide (SEQ ID NO:6);
   and wherein the Tie2 binding peptide monomers are multimerized via a linking moiety, spacer and/or multimerizing agent.

18. A kit comprising (a) a multimeric form of Tie2 binding peptide monomers, (b) an antiviral agent and (c) instructions for use of the kit for treating an animal or cell infected with influenza and/or for treating a bacterial superinfection in an animal or cell infected with influenza; wherein each peptide monomer comprises:
   (i) a T7 peptide (SEQ ID NO:1) or a T7 modified peptide (SEQ ID NO:2);
   (ii) a GA3 peptide (SEQ ID NO:3) or a GA3 modified peptide (SEQ ID NO:4);
   (iii) a T4 peptide (SEQ ID NO:9) or a T4 modified peptide (SEQ ID NO:10);
   (iv) a T6 peptide (SEQ ID NO:7) or a T6 modified peptide (SEQ ID NO:8); or
   (v) a T8 peptide (SEQ ID NO:5) or a T8 modified peptide (SEQ ID NO:6);
   and wherein the Tie2 binding peptide monomers are multimerized via a linking moiety, spacer and/or multimerizing agent.

19. The kit of claim 18, wherein the antiviral agent is amantadine, rimantadine, zanamivir, peramivir, viramidine, ribavirin or oseltamivir.

20. The kit of claim 18, wherein the Tie2 binding peptide monomer comprises a T7 peptide as shown in the amino acid sequences of SEQ ID NOs: 1 or 2 or comprises a GA3 peptide as shown in the amino acid sequences of SEQ ID NOs: 3 or 4.

21. The kit of claim 18, wherein the Tie2 binding peptide monomer comprises a peptide selected from the a group consisting of a T4 peptide, a T6 peptide and a T8 peptide as shown in the amino acid sequences of SEQ ID NOs:5-10.

22. The kit of claim 18, wherein the multimeric form is a dimer, comprising: (a) a first peptide chain; (b) a second peptide chain; and (c) a linking moiety connecting said first and second peptide chains.

23. The kit of claim 22, wherein the first peptide chain is a T7 peptide (SEQ ID NOs: 1 or 2) and/or the second peptide chain is a T7 peptide.

24. The kit of claim 22, wherein the linking moiety comprises one or more polyethylene glycol (PEG) polymers covalently bound to the first peptide chain and the second peptide chain.

25. The kit of claim 18, wherein the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains.

26. The kit of claim 25, wherein the first, second, third and fourth peptide chains are T7 peptides (SE Q ID NOs: 1 or 2).

27. The kit of claim 26, wherein the sinking moiety is PEG, the PEG having a molecular weight of about 10,000 Daltons.

28. The kit of claim 25, wherein the linking moiety comprises one or more branched polyethylene glycol (PEG) polymers covalently bound to the first, second, third and fourth peptide chains, the PEG having a molecular weight in a range of about 3,000 Daltons to about 20,000 Daltons.

* * * * *

UNITED STATES PATENT AND TRADEMARK OFFICE
CERTIFICATE OF CORRECTION

PATENT NO. : 10,314,882 B2
APPLICATION NO. : 14/783261
DATED : June 11, 2019
INVENTOR(S) : Daniel Dumont, Paul Van Slyke and Warren Lee Page 1 of 1

It is certified that error appears in the above-identified patent and that said Letters Patent is hereby corrected as shown below:

In the Claims

In Claim 1, Column 39, Line 23, "(iv) a T6 peptide (SEQ ID NO:7) or a T8 modified peptide..." should read -- (iv) a T6 peptide (SEQ ID NO:7) or a T6 modified peptide... --

In Claim 4, Column 39, Line 39, "...peptide as shown in the amino acid sequences of SE Q ID..." should read -- ...peptide as shown in the amino acid sequences of SEQ ID... --

In Claim 7, Column 39, Lines 51-52, "...peptide (SEQ ID NOs: 1 or 2) and/or the second peptide chain is a T7 peptide (SEC) ID NOs: 1 or 2)." should read -- ...peptide (SEQ ID NOs: 1 or 2) and/or the second peptide chain is a T7 peptide (SEQ ID NOs: 1 or 2). --

In Claim 13, Column 40, Lines 17-18, "The method sf claim 1, for treating a bacterial superinfection..." should read -- The method of claim 1, for treating a bacterial superinfection... --

In Claim 17, Column 40, Lines 41-42, "...and wherein the Tie2 binding peptide monomers are muItimerized..." should read -- ...and wherein the Tie2 binding peptide monomers are multimerized... --

In Claim 26, Column 42, Line 7, "...fourth peptide chains are T7 peptides (SE Q ID NOs: 1 or 2)." should read -- ...fourth peptide chains are T7 peptides (SEQ ID NOs: 1 or 2). --

In Claim 27, Column 42, Line 9, "The kit of claim 26, wherein the sinking moiety is..." should read -- The kit of claim 26, wherein the linking moiety is... --

Signed and Sealed this
Eighth Day of October, 2019

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

His His His Arg His Ser Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Cys His His His Arg His Ser Phe
1               5

<210> SEQ ID NO 3
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 3

Trp Thr Ile Ile Gln Arg Arg Glu Asp Gly Ser Val Asp Phe Gln Arg
1               5                   10                  15

Thr Trp Lys Glu Tyr Lys
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 4

Cys Trp Thr Ile Ile Gln Arg Arg Glu Asp Gly Ser Val Asp Phe Gln
1               5                   10                  15
```

Arg Thr Trp Lys Glu Tyr Lys
            20

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

His Pro Trp Leu Thr Arg His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Cys His Pro Trp Leu Thr Arg His
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Lys Leu Trp Val Ile Pro Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Peptide

<400> SEQUENCE: 8

Cys Lys Leu Trp Val Ile Pro Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Asn Leu Leu Met Ala Ala Ser
1               5

<210> SEQ ID NO 10
<211> LENGTH: 8
<212> TYPE: PRT
<213> ORGANISM: Artificial Sequence

```
<220> FEATURE:
<223> OTHER INFORMATION: Synthetic Peptide

<400> SEQUENCE: 10

Cys Asn Leu Leu Met Ala Ala Ser
1               5
```